(12) United States Patent
Spakevicius et al.

(10) Patent No.: US 9,744,142 B2
(45) Date of Patent: Aug. 29, 2017

(54) FORMULATIONS OF VOLATILE ANESTHETICS AND METHODS OF USE FOR REDUCING INFLAMMATION

(75) Inventors: Danguole Spakevicius, Houston, TX (US); Hatice Ozsoy, Houston, TX (US)

(73) Assignee: Board of Regents, The University of Texas Systems, Austin, TX (US)

( * ) Notice: Subject to any disclaimer, the term of this patent is extended or adjusted under 35 U.S.C. 154(b) by 435 days.

(21) Appl. No.: 13/318,591

(22) PCT Filed: May 5, 2010

(86) PCT No.: PCT/US2010/033746
§ 371 (c)(1),
(2), (4) Date: Mar. 22, 2012

(87) PCT Pub. No.: WO2010/129686
PCT Pub. Date: Nov. 11, 2010

(65) Prior Publication Data
US 2012/0171281 A1    Jul. 5, 2012

Related U.S. Application Data

(60) Provisional application No. 61/175,751, filed on May 5, 2009.

(51) Int. Cl.
| | | |
|---|---|---|
| *A61K 9/127* | (2006.01) |
| *A61K 31/08* | (2006.01) |
| *A61K 9/00* | (2006.01) |
| *A61K 9/107* | (2006.01) |
| *A61K 31/02* | (2006.01) |
| *A61K 33/00* | (2006.01) |
| *A61K 47/20* | (2006.01) |
| *A61K 47/26* | (2006.01) |
| *A61L 26/00* | (2006.01) |
| *A61K 9/08* | (2006.01) |
| *A61K 47/02* | (2006.01) |
| *A61K 47/06* | (2006.01) |
| *A61K 47/22* | (2006.01) |
| *A61K 47/34* | (2017.01) |
| *A61K 47/10* | (2017.01) |
| *A61K 47/16* | (2006.01) |
| *A61K 47/24* | (2006.01) |
| *A61K 47/44* | (2017.01) |

(52) U.S. Cl.
CPC ............ *A61K 31/08* (2013.01); *A61K 9/0014* (2013.01); *A61K 9/08* (2013.01); *A61K 9/107* (2013.01); *A61K 9/127* (2013.01); *A61K 31/02* (2013.01); *A61K 33/00* (2013.01); *A61K 47/02* (2013.01); *A61K 47/06* (2013.01); *A61K 47/20* (2013.01); *A61K 47/22* (2013.01); *A61K 47/26* (2013.01); *A61K 47/34* (2013.01); *A61L 26/0066* (2013.01); *A61K 47/10* (2013.01); *A61K 47/16* (2013.01); *A61K 47/24* (2013.01); *A61K 47/44* (2013.01); *A61L 2300/202* (2013.01); *A61L 2300/402* (2013.01); *A61L 2300/626* (2013.01)

(58) Field of Classification Search
USPC .......................................................... 424/450
See application file for complete search history.

(56) References Cited

U.S. PATENT DOCUMENTS

| | | | |
|---|---|---|---|
| 3,337,400 A | 8/1967 | Smith | |
| 4,622,219 A | 11/1986 | Haynes | |
| 4,744,989 A | 5/1988 | Payne et al. .................. | 424/490 |
| 4,879,062 A | 11/1989 | Moore ........................ | 252/315.1 |
| 5,091,188 A * | 2/1992 | Haynes ........................ | 424/450 |
| 5,874,469 A | 2/1999 | Maniar et al. ................ | 514/550 |
| 6,197,323 B1 | 3/2001 | Georgieff | |
| 2003/0045766 A1 | 3/2003 | McKim et al. | |
| 2004/0127578 A1 | 7/2004 | Trillo et al. | |
| 2005/0215533 A1 | 9/2005 | Gottlieb et al. | |
| 2006/0067952 A1 | 3/2006 | Chen ............................ | 424/400 |
| 2006/0198891 A1 | 9/2006 | Ravenelle et al. ............ | 424/486 |
| 2006/0228383 A1 | 10/2006 | Pacheco et al. | |
| 2007/0104796 A1 | 5/2007 | Franks et al. | |
| 2008/0119820 A1 | 5/2008 | Phan et al. | |
| 2008/0234389 A1 | 9/2008 | Mecozzi et al. .............. | 514/722 |
| 2011/0039944 A1 | 2/2011 | Capelli et al. | |
| 2011/0159078 A1 | 6/2011 | Burton et al. | |
| 2011/0269843 A1 | 11/2011 | Phan et al. | |
| 2013/0273141 A1 | 10/2013 | Burton et al. | |

FOREIGN PATENT DOCUMENTS

| | | |
|---|---|---|
| CA | 2 283 227 | 9/1998 |
| EP | 0 864 329 | 9/1998 |
| JP | S60-501557 | 9/1985 |
| JP | H10-251142 | 9/1998 |
| JP | 2003-520769 | 8/2003 |
| JP | 2005-539004 | 12/2005 |
| JP | 2006-504740 | 2/2006 |

(Continued)

OTHER PUBLICATIONS

Itah et al., "A replacement for methoxyflurane (Metofane) in open-circuit anaesthesia," *Laboratory Animals*, 38:280-285, 2004.
Office Action issued in Chinese Application No. 201080030510.3, issued Mar. 4, 2013.
Lee et al., "Anti-inflammatory and antinecrotic effects of the volatile anesthetic sevoflurane in kidney proximal tubule cells," *Am J Physiol Renal Physiol*, 2006, 291:F67-F78.
Rock et al., "Effect of Halothane on the $Ca^{2}$-Transport System of Surface Membranes Isolated from Normal and Malignant Hyperthermia Pig Skeletal Muscle," *Archives of Biochemistry and Biophysics*, Aug. 1987, 265(2):703-707.

(Continued)

*Primary Examiner* — Dennis J Parad
(74) *Attorney, Agent, or Firm* — Parker Highlander PLLC

(57) ABSTRACT

The present invention provides methods for treating inflammation or a wound in a subject in need of such wound treatment or inflammation treatment by delivering a volatile anesthetic to the wound or the inflammation site.

2 Claims, 1 Drawing Sheet

(56) References Cited

FOREIGN PATENT DOCUMENTS

| WO | WO 2008-036858 | 3/2008 |
|---|---|---|
| WO | WO 2009/094460 | 7/2009 |

OTHER PUBLICATIONS

Petersen-Felix, et al., "Analgesic effect in humans of subanaesthetic isoflurane concentrations evaluated by experimentally induced pain," *British Journal of Anaesthesia*, 1995, 75:55-60.

Written Opinion of the International Searching Authority dated Jul. 9, 2010 for PCT/US10/33746.

Extended European Search Report and Search Opinion issued in European Application No. 10772774.5, mailed Oct. 24, 2012.

Ardente et al., "Vehicle effects on in vitro transdermal absorption of sevolurane in the bullfrog, Rana catesbeiana," *Environmental Toxicology and Pharmacology*, 25:373-379, 2008.

Fast et al., "Fluoropolymer-based emulsions for the intravenous delivery of sevoflurane," *Anesthesiology*, 109:651-6, 2008.

Office Communication issued in U.S. Appl. No. 12/863,757, dated Jun. 22, 2012.

Parlato et al., "Synthesis, characterization, and applications of hemifluorinated dibranced amphiphiles," *J. Org. Chem.*, 76:6584-6591, 2011.

Zhou et al., "The efficacy and safety of intravenous emulsified isoflurane in rats," *Anesth. Analg.*, 102:129-34, 2006.

Giraud et al., "Halothane reduces the early lipopolysaccharide-induced lung inflammation in mechanically ventilated rats," *American Journal of Respiratory and Critical Care Medicine*, 162:2278-2286, 2000.

Office Action issued in European Application No. 10 772 774.5, mailed Apr. 10, 2014.

Sanchez-Conde et al., "The comparative abilities of propofol and sevoflurane to modulate inflammation and oxidative stress in the kidney after aortic cross-clamping," *Anesthesia & Analgesia*, 106(2):371-378, 2008.

Sopka et al., "Effects of xenon and isoflurane on apoptosis and inflammation in a porcine myocardial infarction model," *Annals of Anatomy*, 195:166-174, 2013.

Office Action issued in Japanese Application No. 2012-509051, mailed Jun. 19, 2014, and English language translation thereof.

Haynes et al., "Long duration local anesthesia with lecithin-coated microdroplets of methoxyflurane: studies with human skin," *Regional Anesthesia*, 16:173-180, 1991.

Office Action issued in Australian Application No. 2010245932, mailed Feb. 20, 2015.

Office Action issued in Canadian Application No. 2,760,775, mailed Feb. 12, 2016.

Office Action issued in Chinese Application No. 201080030510.3, mailed Feb. 16, 2016.

* cited by examiner

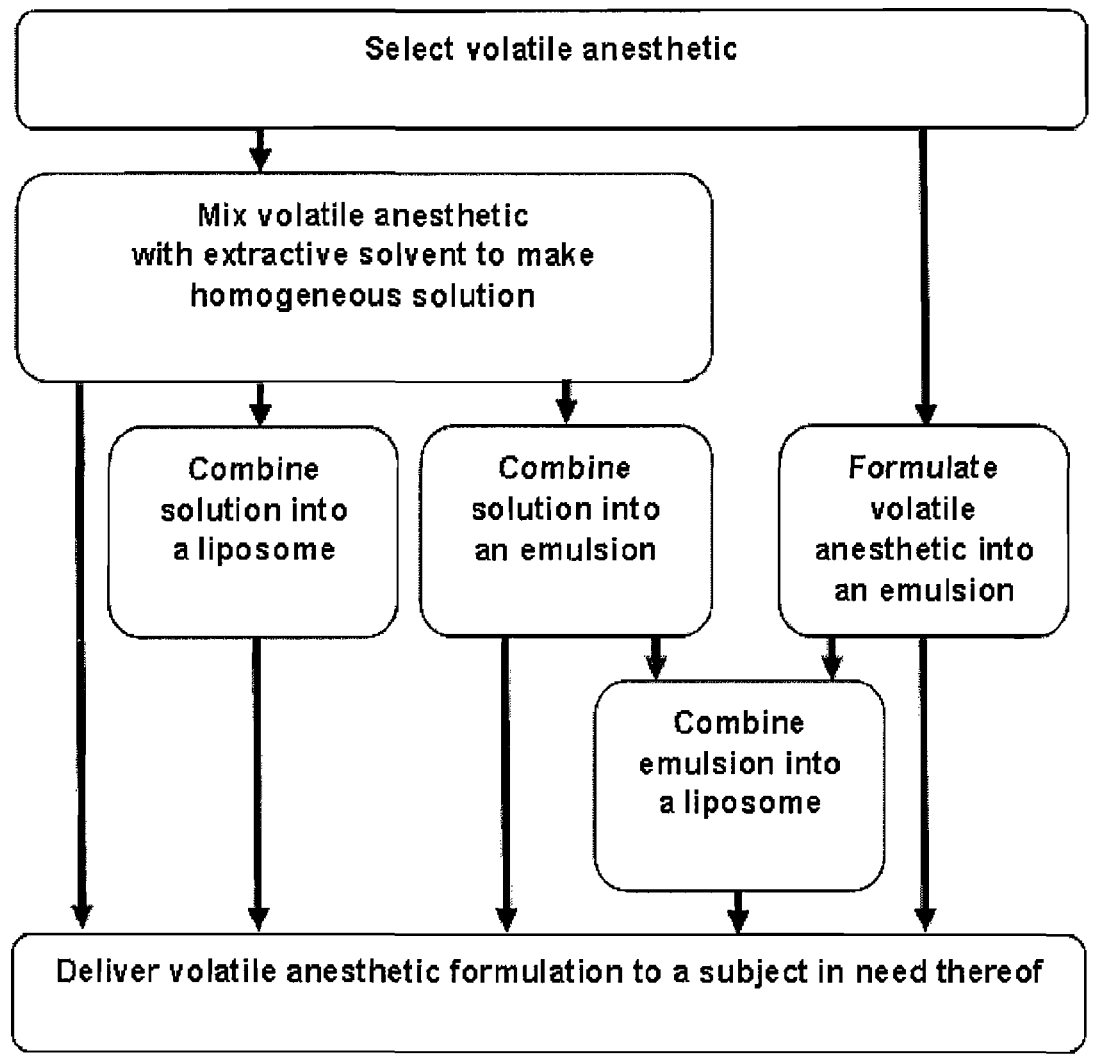

FORMULATIONS OF VOLATILE ANESTHETICS AND METHODS OF USE FOR REDUCING INFLAMMATION

CROSS-REFERENCE TO RELATED APPLICATION

The present application is a 35 U.S.C. §371 national phase application from and claiming priority to, International Application No. PCT/US2010/33746, filed May 5, 2010, and published under PCT Article 21(2) in English, which is entitled to priority under 35 U.S.C. §119(e) to U.S. Provisional Application No. 61/175,751, filed May 5, 2009, all of which applications are hereby incorporated by reference herein in their entireties.

BACKGROUND OF THE INVENTION

Inflammation is a vital protective mechanism in mammals, helping minimize the impact of injurious stimuli on the structure and function of mammalian systems affected by such stimuli. In a simplistic description of the inflammatory process, the body's white blood cells, chemicals (inflammatory mediators) and plasma rush to the area affected by foreign substances such as bacteria, viruses and other harmful stimuli. This mobilization helps protect mammals from infection and injury, but may also trigger a cascade of events leading up to physiological sequelae.

Inflammation may be acute or chronic. The acute form of inflammation may last from a few minutes to a few days. The chronic form of inflammation, which may last from months to years, may impact and change the cells in affected area. Inflammation plays a critical role in wound healing, for example. At times, however, the body's extended inflammatory response may cause chronic wounds, or take place even in the absence of foreign substances, causing damage to its own tissues. At other times, extended/prolonged response of this protective mechanism results in discomfort of functional or cosmetic nature. In these situations, methods of containing or reversing inflammation may have to be employed.

Inflammation is believed to be a major mediator of a wide range of acute and chronic diseases. Such misdirected inflammation is present in many diseases, such as arthritis, tendonitis, bursitis and similar conditions. Inflammation may affect organs as part of an autoimmune disorder. The types of symptoms depend on which organs are affected. Examples include inflammation of the heart (myocarditis, which may cause chest pain or fluid retention), inflammation of the small tubes that transport air to the lungs (bronchiolitis, which may cause shortness of breath similar to an asthma attack), inflammation of the kidneys (nephritis, which may cause high blood pressure or kidney failure), inflammation of the large intestine (colitis, which may cause cramps and diarrhea), inflammation of the eye (iritis or uveitis, which may cause pain or decreased vision), inflammation of the muscles (polymyositis, which may cause achiness or weakness), and inflammation of the blood vessels (vasculitis, which may cause rash, headaches, or internal organ damage). Pain may not be a main symptom of these inflammatory syndromes since many organs have very few pain-sensitive nerves. Treatment of organ inflammation should be directed at the cause of inflammation whenever possible.

Although inflammation is a necessary part of the body's defense system, excessive, prolonged or misdirected inflammation may result in chronic diseases that may be debilitating. Current treatment options are limited and include anti-inflammatory drugs which are mainly comprised of non-steroidal anti-inflammatory drugs (NSAIDs) and corticosteroids, but the chronic administration of these compounds often cause problems in patients. Healthcare professionals lack any alternative with better safety and side-effects profiles than these compounds.

Volatile anesthetics have been used safely for decades as general anesthetics. Besides producing analgesia, volatile anesthetics affect other receptors and have been shown to have anti-inflammatory and muscle relaxing properties when administered by inhalation and in vitro. Volatile anesthetics have been shown to reduce cytokine production and release in both in vivo and in vitro inflammation model, and downregulate lipopolysaccharide (LPS)-induced production of pro-inflammatory cytokines. Additionally, volatile anesthetics have been shown to inhibit neutrophil function and decrease time to resolution of inflammation. However, volatile anesthetics have not been successfully used in the local treatment of inflammation.

There is a need in the art for improved formulations that may be used in the treatment of inflammation. There is also a need in the art for improved methods for treating misdirected or prolonged inflammation. The current invention fulfills these needs.

SUMMARY OF THE INVENTION

The invention includes a pharmaceutically acceptable composition comprising a metered amount of a volatile anesthetic dissolved in an aqueous solution in an amount effective to treat a wound, wherein the solution further comprises at least one extractive solvent in an amount effective to reduce volatility of the volatile anesthetic, wherein the solution is a component of an emulsion, wherein the composition further comprises a pharmaceutically acceptable excipient.

In this and other embodiments disclosed herein, the at least one extractive solvent is selected from the group consisting of dimethyl sulfoxide (DMSO), N-methyl-2-pyrrolidone (NMP), dimethylformamide, dimethylacetamide, dimethylisosorbide, ethanol, propanol, PEG-400, PEG-300, diethylene glycol monoethyl ether, and isopropanol. Preferably, the at least one extractive solvent comprises from about 0.1% to about 75% of the solution, and the composition is sterile.

In this and other embodiments disclosed herein, the composition is formulated for an administration by a route selected from the group consisting of topical, intrathecal, epidural, transdermal, topical, oral, intra-articular, mucosal, buccal, rectal, vaginal, intramuscular, intravesical and subcutaneous.

Preferably, the volatile anesthetic is selected from the group consisting of isoflurane, halothane, enflurane, sevoflurane, desflurane, methoxyflurane, xenon and mixtures thereof, and more preferably, the volatile anesthetic is isoflurane.

Preferably, the emulsion comprises a lipid, and the lipid comprises soybean oil, olive oil, peanut oil, castor oil, corn oil or sesame oil. The emulsion may further comprises an emulsifier.

In addition, the volatile anesthetic is preferably in the form of a suspension, a cream, a paste, an oil, a lotion, a gel, a foam, a hydrogel, an ointment, a liposome, an emulsion, a liquid crystal emulsion, and a nano-emulsion.

The composition may further comprises an antibiotic.

In this and other embodiments disclosed herein, the solution comprises at least one constituent selected from the group consisting of water, a saline solution, and an artificial cerebrospinal fluid.

Further included in the invention is a pharmaceutically acceptable composition comprising a metered amount of a volatile anesthetic emulsion.

Also included is a pharmaceutically acceptable composition comprising a metered amount of a volatile anesthetic dissolved in a solution in an amount effective to treat a wound, wherein the solution further comprises at least one extractive solvent in an amount effective to reduce volatility of the volatile anesthetic, wherein the composition further comprises a solubilizing agent, wherein the composition further comprises a pharmaceutically acceptable excipient.

In addition, there is included a pharmaceutically acceptable composition comprising a metered amount of a micro-droplet suspension, wherein the micro-droplet suspension comprises a sphere of a volatile anesthetic surrounded by a stabilizing layer of a phospholipid, wherein the composition further comprises a pharmaceutically acceptable excipient. In one aspect, the diameter of the microdroplet ranges from about 200 Angstroms up to about 10,000 Angstroms. In another aspect, the micro-droplets are produced by sonication, homogenization, microfluidization or other processes involving high shear, wherein the ratio of the volume of the volatile anesthetic to the weight of the phospholipid layer is at least 1.0 ml/g and the composition contains at least 3% w/v of the volatile anesthetic.

Also included is a pharmaceutically acceptable composition comprising a metered amount of a volatile anesthetic dissolved in an aqueous solution in an amount effective to treat a wound, wherein the solution is a component of an emulsion, wherein the composition further comprises a pharmaceutically acceptable excipient.

The invention further includes a method of treating a wound in a subject in need thereof, the method comprising topically administering to the wound of the subject a volatile anesthetic dissolved in a solution in an amount effective to treat the wound, wherein the solution further comprises at least one extractive solvent in an amount effective to reduce volatility of the volatile anesthetic, wherein the solution is a component of an emulsion, wherein the administration is not by inhalation. The administration is by an intravenous route, or is not by an intravenous route. Further, the administration is topical, transdermal, intrathecal, epidural, mucosal, intramuscular, subcutaneous, oral, rectal, vaginal, buccal, intra-articular or intravesical.

Also included is a method of treating a wound in a subject in need thereof, the method comprising topically administering to the wound of the subject a volatile anesthetic dissolved in a solution in an amount effective to treat the wound, wherein the solution further comprises at least one extractive solvent in an amount effective to reduce volatility of the volatile anesthetic, wherein the composition further comprises a solubilizing agent, wherein the administration route is not by inhalation.

In addition, there is included a method of treating a wound in a subject in need thereof, comprising topically administering to the wound of the subject a volatile anesthetic dissolved in a solution in an amount effective to treat the wound, wherein the solution is a component of an emulsion, wherein the administration route is not inhalation, method of claim 67, wherein the administration route is not intravenous.

Further included is a method of treating a wound in a subject in need thereof comprising topically administering to the wound of the subject a liposome suspension comprising a volatile anesthetic in an amount effective to treat the wound, wherein the administration route is not inhalation.

Also included in the invention is a method of treating or reducing inflammation in a subject in need thereof, the method comprising topically administering to the subject a volatile anesthetic dissolved in a solution in an amount effective to treat or reduce the inflammation, wherein the solution further comprises at least one extractive solvent in an amount effective to reduce volatility of the volatile anesthetic, wherein the administration route is not inhalation. Preferably, the inflammation is associated with arthritis, tendonitis, bursitis, colitis, inflammatory bowel disease, iritis, polymyositis, interstitial cystitis, inflammatory chronic prostatitis, inflammatory breast cancer (IBC) or vasculitis. In certain embodiments, the inflammatory bowel disease is ulcerative colitis or Crohn's disease.

The invention also includes a method of treating or reducing inflammation in a subject in need thereof, the method comprising topically administering to the wound of the subject a micro-droplet suspension comprising a sphere of a volatile anesthetic surrounded by a stabilizing layer of a phospholipid in an amount effective to treat the wound, wherein the administration route is not inhalation.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 illustrates a flowchart representing general methods for making compositions for the delivery of a formulated volatile anesthetic to the affected area of a subject.

DETAILED DESCRIPTION OF THE INVENTION

The present invention relates to the discovery that the compositions and methods of the invention are useful to treat or reduce inflammation associated with wounds, autoimmune diseases or any other pathological conditions, involving or due to inflammation. In one aspect, the compositions and methods of the present invention may be used to reduce or eliminate inflammation in a subject and thereby aid in the recovery from disease or condition involving inflammation. In another aspect, the invention includes a method of treating or reducing inflammation in a subject in need of such treatment, wherein a composition of the invention is administered to the subject by an administration route other than inhalation. In yet another aspect, the administration route comprises intravenous administration. In yet another aspect, the administration route does not comprise intravenous administration.

The compositions and methods of the invention may be used to reduce acute or chronic inflammation associated with diseases or conditions, including but not limited to arthritis, tendonitis, bursitis, colitis, inflammatory bowel disease (including ulcerative colitis and Crohn's disease), iritis, polymyositis, interstitial cystitis, inflammatory chronic prostatitis, inflammatory breast cancer (IBC) and vasculitis.

The present invention provides compositions comprising volatile anesthetic and methods for administering compositions comprising volatile anesthetics to treat wounds and reduce or eliminate inflammation in targeted areas of the body (including but not limited to joints, organs, tissue, cartilage) in a subject, such as a human, animal patient or laboratory animal such as a mouse or rat, in need of such treatment, wherein the route of administration is not by inhalation.

In one embodiment, the present invention provides a composition comprising a volatile anesthetic formulated in a solution. In another embodiment, the present invention provides a composition comprising a volatile anesthetic formulated in a solution, wherein the solution further comprises a pharmaceutically acceptable extractive solvent, for example, but not limited to, DMSO.

In one embodiment, the present invention provides a composition comprising a volatile anesthetic formulated in a solution, wherein the solution is a component of an emulsion. In another embodiment, the present invention provides a composition comprising a volatile anesthetic formulated in a solution, wherein the solution comprises a pharmaceutically acceptable extractive solvent, and wherein the solution is a component of an emulsion.

In one embodiment, the present invention provides a composition comprising a volatile anesthetic formulated in a solution, wherein the solution is a component of a liposome. In another embodiment, the present invention provides a composition comprising a volatile anesthetic formulated in a solution, wherein the solution comprises a pharmaceutically acceptable extractive solvent, for example, but not limited to, DMSO, and wherein the solution is a component of a liposome.

The acceptable extractive solvents may include, but are not limited to, vehicles and functional components. Examples of vehicles include, but are not limited to, polyethylene glycol 300 and polyethylene glycol 400. Examples of functional components include, but are not limited to, diethylene glycol monoethyl ether, polypropylene glycol dicaprylocaprate, and DMSO.

In one aspect, the presence of an extractive solvent in the composition of the invention comprising the volatile anesthetic may provide substantial advantages, including improving the physical characteristics, pharmacological properties, and/or the ease of use of the composition. The extractive solvent may interact with the volatile anesthetic (in a non-limiting example, isoflurane) in a non-azeotropic fashion to effectively reduce vaporization or evaporation of the volatile anesthetic. This effect of reducing volatility may be referred to as volatility attenuating effect (VAE). In this way, the shelf-life, durability, and/or ease of use of a volatile anesthetic composition may be improved.

In one aspect, the pharmacokinetics of the volatile anesthetic may be altered by the presence of an extractive solvent. For example, without wishing to be bound by any theory, the extractive solvent may function in certain embodiments as a reservoir for the volatile anesthetic such that the amount of volatile anesthetic retained and/or the duration of retention is enhanced as compared to the application of pure non-formulated volatile anesthetic. Hence an extractive solvent renders delivery of the volatile anesthetic to a particular site of action more effective. Similarly, in certain embodiments where the volatile anesthetic composition contains an extractive solvent, the extractive solvent may facilitate absorption, in terms of rate and/or extent, of the volatile anesthetic into the site of action. Additionally, presence of an extractive solvent may have additive or synergistic contributions to the volatility attenuation effect (VAE) rendered by the vehicle. In this aspect, the formulation may facilitate retention of the volatile anesthetic, which otherwise would be prone to rapidly escape from the site of action due to its highly volatile nature, even at room temperature.

In one aspect, when the formulation is a component of an emulsion or of a liposome, the emulsion or the liposome may function as a reservoir for the volatile anesthetic to retain the volatile anesthetic in a particular region more effectively and/or help deliver the volatile anesthetic to site(s) of action. In yet another aspect, the delivery of the volatile anesthetic may be tailored as a sustained release. This may eliminate or reduce the need for repeated dosing, and/or allow the achievement of the desired steady-state drug levels. Reduced volatility of the volatile anesthetic in composition may also improve the ease of handling the volatile anesthetic compositions. This may facilitate manufacturing and packaging the compositions of the invention. This may also avoid the possibility of inhalation of the volatile anesthetic by the patient, health care provider or packaging facility worker. Further, the reduced vaporization of a volatile anesthetic in solution due to the presence of an extractive solvent may also reduce any potential concerns of a possible risk of fire and/or exposure at the medical facility.

In one aspect, the present invention relates to a method for reducing inflammation associated with a wound, autoimmune disease or any other disease or condition involving or resulting from inflammation in a subject in need thereof, comprising administering a therapeutically effective amount of a composition of the invention to the affected area of the subject by an administration route other than inhalation. The volatile anesthetic is dissolved in a solution comprising an extractive solvent in an amount effective to reduce inflammation. Preferred volatile anesthetics are the halogenated ether volatile anesthetics dissolved in a pharmaceutically acceptable solution. In one embodiment, the volatile anesthetic is a component of an emulsion or of a liposome.

The methods preferably comprise topical, subcutaneous, transdermal, oral, rectal, mucosal, vaginal, buccal, rectal, intra-articular and intravesical delivery of a volatile anesthetic in a composition. Also preferred routes of administration include intrathecal, epidural, and intramuscular. In some embodiments, the volatile anesthetic is a component of an emulsion or of a liposome. In addition, the amount administered is an amount effective to aid in wound healing, auto-immune disease or any other disease or conditions, involving or resulting from inflammation.

In certain embodiments, a volatile anesthetic in solution is delivered to a specific site of a subject prior to wound creation, such as prior to a surgery or other medical procedure. The volatile anesthetic may be a halogenated volatile anesthetic selected from the group consisting of isoflurane, halothane, enflurane, sevoflurane, desflurane, methoxyflurane, xenon and mixtures thereof. Many of these agents are racemic mixtures. In some embodiments, the racemic mixtures are used. In other embodiments, only the d-isomer or the l-isomer of an agent is used (for examples, see U.S. Pat. Nos. 5,114,715; 5,114,714 and 5,283,372). In certain embodiments, isoflurane is used. The solution, such as an isoflurane solution, may be prepared in a concentration of about 5 ng/ml solution to about 100 ng/ml solution. The solution may comprise from about 1% to about 99% v/v, from about 5% to about 70% v/v, or about 50% v/v, or about 25% v/v, or about 10% v/v volatile anesthetic in solution. The volatile anesthetic may be isoflurane and/or the solution may comprise polyethylene glycol 400, polyethylene glycol 300, diethylene glycol monoethyl ether, polypropylene glycol dicaprylocaprate, water, saline or artificial cerebrospinal fluid. In certain embodiments, the solution may be a component of an emulsion, which may further comprise an extractive solvent. In other embodiments, the solution may be a component of an liposome, which may further comprise an extractive solvent. When administered topically to an affected area, it is desirable to achieve a clinically effective concentration, which in some, but not necessarily all, cases may range, for example, from about 5 mcg/ml to about 2,000,000 mcg/ml of active agent in a formulation. In other embodiments, in topical administration it is desirable to achieve a clinically effective concentration, which in some, but not necessarily all, cases may range, for example, from about 2 microliters to about 50 microliters of solution per centimeter square of area of application. In another embodiment, volatile anesthetic formulation may be administered orally or rectally. In another embodiment, orally or rectally administered formulation may deliver volatile anesthetic to a specific site, for example, colon. In yet another embodiment, orally or rectally administered formulation may release volatile anesthetic in sustained release fashion over a period of time ranging from a few minutes to several hours. The delivery of the active agent may be continuous, periodic, a one-time event, or the active agent may be both periodically administered and continuously administered to the subject on separate occasions.

Preferably, since the solution is intended for administration to wounds or other sites of action in need of reduction in inflammation associated with autoimmune diseases or any other pathological condition, the solution comprising the volatile anesthetic is sterile. This may be achieved by ensuring that all starting materials are sterile and maintaining them under sterile conditions prior to administration. This may also be achieved by incorporation of an antimicrobial filter as has been done with various types of infusions (see, for example, U.S. Pat. No. 5,695,490). As for the underlying solution, the nature of the solution is not believed to be critical, and solutions comprising polypropylene glycol 400 (or the like), diethylene glycol monoethyl ether, normal saline or even solutions formulated to mimic natural body fluids, such as artificial cerebrospinal fluids, are contemplated.

Yet another aspect of the present invention involves a sealed container comprising a volatile anesthetic solution of the present invention. The interior of the container may be sterile. The container may be, for example, a syringe, a plastic bag, a collapsible plastic bag, a glass bottle, a glass ampoule or a plastic bottle. The container may be itself a wound dressing or part of a wound dressing. In another aspect of present invention, a container that offers many advantages, such as, for example, ease of application, unit dose configuration, and excellent container-closure compatibility profile, is contemplated. This container may be such that the volatile anesthetic solution is contained in a crushable sealed ampoule. The ampoule is in turn enclosed in protective covering on which pressure is applied to crush the ampoule, which then releases volatile anesthetic solution for percolation through a flint-type tip which capped the ampoule in protective covering. When such packaging configuration is employed, care is taken to leave as little as possible or ideally no headspace in ampoule for the volatile anesthetic to escape and cause a change in solution composition over a period of shelf life.

The present invention overcomes limitations in the art by providing improved volatile anesthetic compositions comprising a volatile anesthetic formulated in a solution. In some embodiments, the solution further comprises a pharmaceutically acceptable extractive solvent. The presence of the extractive solvent may provide certain advantages for the volatile anesthetic composition, including a reduction in the anesthetic vapors emitted from the solution (for example, reducing risks associated with the any possible flammability of the vapors and/or inhalation by patient or medical personnel), improvements in the shelf-life or durability of the composition, and/or improved pharmacokinetics of the volatile anesthetic composition. For example, the extractive solvent may interact with the volatile anesthetic (for example, isoflurane) in a non-azeotropic fashion to effectively reduce vaporization or evaporation of the volatile anesthetic (i.e., volatility attenuating effect, VAE). In this way, the shelf-life and/or durability of a volatile anesthetic in solution may be improved. Additionally, the pharmacokinetics of the volatile anesthetic may be altered by the extractive solvent, which can also interact with the volatile anesthetic in a non-azeotropic fashion to effectively reduce vaporization or evaporation of the volatile anesthetic. Such interaction, when and if present, would further enhance VAE rendered by the vehicle. For example, without wishing to be bound by any theory, the extractive solvent may function in certain embodiments as a reservoir for the volatile anesthetic to maintain the volatile anesthetic in a particular region more effectively and/or help deliver the volatile anesthetic to site(s) of action. In various embodiments, the presence of an extractive solvent in the volatile anesthetic solution may also allow for mixing the solution prior to administration without the use of a sonicator.

The present invention also provides methods for using such volatile anesthetic compositions for reducing inflammation in a subject in need of such reduction of inflammation. Specifically, although agents, such as volatile anesthetics, have been delivered by inhalation to produce general anesthesia, volatile anesthetics may be formulated in a solution and delivered regionally or locally (for example, orally, intra-articularly, transdermally, topically, mucosally, buccally, rectally or vaginally, etc.) to reduce or inhibit inflammation. In general, the methods may involve the delivery of a volatile anesthetic in solution, which in certain embodiments may be a component of a solution, an emulsion or a liposome, to the subject in an amount effective to reduce inflammation. The present invention may be used for management of chronic or acute inflammation. In other embodiments, the volatile anesthetic may be delivered to a subject to treat at least a portion of the subject prior, during, or after a surgery or other medical procedure.

Extractive Solvents

The volatile anesthetic compositions of the present invention may contain a solvent, such as an extractive solvent, in combination with a volatile anesthetic. The phrase "extractive solvent," as used herein, refers to a solvent which may interact with a volatile anesthetic in the compositions of the invention to reduce the volatility of the volatile anesthetic without chemically reacting to the anesthetic. This phrase also includes compounds that do not necessarily extract, including vehicles and functional components, which may affect properties such as, but not limited to, permeability or penetration.

Certain extractive solvents interact in a non-azeotropic fashion with a volatile anesthetic. Nonetheless, the term "extractive solvent," as used herein, may include certain compounds, or mixtures thereof, which interact with a volatile anesthetic to form an azeotropic or pseudoazeotropic solution as long as the vapor pressure or evaporation of the volatile anesthetic from the solution is reduced. Extractive solvents are also expected to attenuate volatility of volatile anesthetics such that the time required for a given amount of anesthetic to escape from a given surface at a given temperature is increased, resulting in appreciable increase in time of contact of volatile anesthetic with the site of application before complete evaporation of unabsorbed portion, as compared with the application of pure volatile anesthetic under similar conditions. In another embodiment, formulations of current invention may contain an extractive solvent such that this extractive solvent enhances permeability of volatile anesthetic into the tissue of interest thus favoring either achievement of or enhancement of an intended pharmacological outcome. By way of example, but not limitation, the tissue of interest described above may be skin or any other tissue involved or believed to be involved, directly or indirectly, in the intended pharmacological outcome. Enhanced permeability, as it applies to current invention, refers to increase in: (a) amount of volatile anesthetic delivered to the tissue of interest, and/or (b) rate of delivery (i.e., rapid delivery) to the tissue of interest, and/or (c) residence time of volatile anesthetic in the tissue of interest. Increase in residence time refers to a delay in elimination of volatile anesthetic from tissue of interest.

As described below by chemical class as well as individual examples, various extractive solvents are envisioned for use with the present invention. The chemical classes contemplated in this invention comprise fatty alcohols, fatty acids, fatty amines, fatty acid esters, polyols, terpenes, esters, ethers, alkoxylated amides, poly propylene glycol ethers, polyethylene glycols, poly propylene glycols and poly propylene glycol ethers. Selected examples of individual ingredients contemplated in current invention comprise of polyethylene glycol 400, polyethylene glycol 300, diethylene glycol monoethyl ether, Labrasol, oleoyl macrogolglycerides (Labrafil M 1944), linoleoyl macrogolglycerides (Labrafil M2125), lauroyl macrogoglycerides (Labrafil M 2130), propylene glycol dicaprylocaprate, propylene glycol monocaprylate (Capryol 90, Capryol PGMC), polypropylene glycol monolaurate (Lauroglycol 90, Lauroglycol FCC), polyglyceryl-3-dioleate, Peceol, isostearyl isostearate, propylene glycol dipelargonate, polyglyceryl-3 dioleate, propylene glycol dipelargonate, octyldodecyl myristate, diethyl sebacate, diisopropyl adipate, ethyl oleate, glyceryl isostearate, isopropyl isostearate, isopropyl myristate, isostearyl alcohol, isostearic acid, oleyl alcohol, eicosapentanoic acid, docosahexaenoic acid, olive oil, peanut oil, soybean oil, castor oil, corn oil, cottonseed oil, peppermint oil, safflower oil, sesame oil, soybean oil, hydrogenated soybean oil, hydrogenated vegetable oil, medium chain triglycerides coconut oil, palm oil, liquid lanolin, DMSO, NMP, and the like.

The exact concentration of an extractive solvent may be determined empirically and may vary according to the specific volatile anesthetic used. In certain embodiments, the extractive solvent will be present in the composition in an amount effective to reduce volatility of the volatile anesthetic in the composition. Particular care should also be taken to select a concentration of an extractive solvent which results in little or no toxicity when administered. It will be understood that, although certain extractive solvents may exhibit properties which might be used in various separation procedures (e.g., extractive distillation), extractive solvents according to embodiments of the present invention are preferably included in pharmacological mixtures or solutions comprising a volatile anesthetic in order to reduce the volatility of, rather than "extract," the volatile anesthetic.

Including an extractive solvent in an anesthetic composition may increase the ease with which one may mix the solution prior to administration. For example, in certain embodiments, mixing prior to administration may be desirable if final formulation is selected to be self-emulsifying drug delivery system (SEDDS). In certain embodiments, sonication of the anesthetic solution prior to administration is not required when an extractive solvent is included in the volatile anesthetic composition. This advantage may be particularly useful in instances (e.g., chronic administration) where the presence of a sonicator could be noisy or distracting, such as an operating room, and the elimination in the noise of a sonicator may also create an improved environment for a conscious patient receiving a volatile anesthetic composition, e.g., chronically or intermittently for pain relief. Eliminating the need for a sonicator, or other similar device, may also be particularly useful for reducing costs associated with administration of a volatile anesthetic composition according to the present invention. The reduction in the bulk associated with the presence of a sonicator may beneficially improve patient mobility. For example, in instances where a patient may receive repeated administrations of an anesthetic composition via a pump for analgesia, the reduced amount of equipment may improve mobility since the patient is not required to additionally move a sonicator. In certain embodiments, sonication of the anesthetic solution prior to administration is required when an extractive solvent is included in the volatile anesthetic composition.

Extractive solvents are known in the art and are typically used in extractive distillation for separating compounds with similar boiling points by retarding the vapor pressure of the principal component, thereby making possible an efficient separation which would not at all occur in the absence of such solvent. For example, U.S. Pat. No. 5,230,778 describes the purification of isoflurane by extractive distillation using extractive solvents such as dimethylformamide. U.S. Pat. No. 5,336,429 describes solvents for cleaning electronic components and for degreasing metals comprising isoflurane and a lower alcohol or an ester, although these compositions are described as azeotropic mixtures with virtually constant boiling points. In contrast, the present invention provides pharmaceutical preparations, for example, for treating wounds and/or diminishing inflammation. An further aspect of the compositions and methods of the invention for the treatment of wounds and inflammation is the analgesic activity contributed by the volatile anesthetics.

Certain extractive solvents known in the art, such as acetone as described in U.S. Pat. No. 5,230,778, may be sufficiently toxic to limit their inclusion in pharmaceutical preparations at higher concentrations.

In certain embodiments, an extractive solvent may interact as an azeotropic mixture with an anesthetic and reduce the volatility of the anesthetic. For example, ethanol may interact in an azeotropic fashion with a volatile anesthetic as described in U.S. Pat. No. 5,230,778.

Various concentrations of an extractive solvent may be used with the present invention. For example, a composition of the present invention comprising a volatile anesthetic may comprise about 0.1%-99%, 0.1%-60%, 5%-50%, 10%-40%, 5%-25%, 10%-30%, 10%-25%, 25%-50%, 10%-75%, 25%-75%, 10%-65%, 25%-65%, 10%-60%, 25%-60%, 0.1%, 1%, 5%, 10%, 20%, 25%, 30%, 35%, 40%, 45%, 50%, 55%, 60%, 65%, 70%, 75%, 80%, or any range derivable therein, of an extractive solvent.

In certain embodiments, the extractive solvent is polyethylene glycol 400 (PEG 400) or polyethylene glycol 300 (PEG 300). In other embodiments, vehicle is olive oil or peanut oil or liquid lanolin or diethylene glycol monoethyl ether.

In certain embodiments, the extractive solvent is diethylene glycol monoethyl ether. In other embodiments, functional component is ethyl oleate, glyceryl isostearate, isopropyl isostearate, isopropyl myristate, isostearyl alcohol, isostearic acid or oleyl alcohol.

In certain embodiments, the extractive solvent is dimethylsulfoxide (DMSO) or N-methyl-2-pyrrolidone (NMP). In other embodiments, an extractive solvent such as dimethylformamide, dimethylacetamide, or dimethylisosorbide may be used. In instances where acetone is used, care should be taken to choose an appropriate dose in order to minimize any possible toxicity.

Other extractive solvents include PEG-400, PEG-300, and diethylene glycol monoethyl ether.

In various embodiments, it is envisioned that a medically acceptable alcohol, such as ethanol, propanol, or isopropanol may be used. In these embodiments, the concentration of the alcohol used is sufficiently dilute in solution such that little or no irritation or neuron death occurs as a result of injection of the solution near a nerve.

A single extractive solvent, or multiple extractive solvents, may be present in an anesthetic composition of the present invention. For example, in certain embodiments, only a single extractive solvent (e.g., DMSO, NMP or PEG 400) is present in a composition comprising a volatile anesthetic. In other embodiments, two, three, four or more extractive solvents may be present in a composition comprising a volatile anesthetic. In certain embodiments, only a single volatile anesthetic (e.g., isoflurane) is present in an anesthetic composition of the present invention; in other embodiments, two, three, four or more volatile anesthetics may be present in an anesthetic composition of the present invention. In certain embodiments, only a single extractive solvent (e.g., diethylene glycol monoethyl ether) is present in an anesthetic composition of the present invention. In other embodiments, two, three, four or more extractive solvents may be present in an anesthetic composition of the present invention.

N-methylpyrrolidone:

N-methyl-2-pyrrolidone (NMP) is a solvent that may be included in the volatile anesthetic compositions according to the present invention. NMP is a chemical compound with 5-membered lactam structure. It is a clear to slightly yellow liquid miscible with water and solvents including ethyl acetate, chloroform, benzene and lower alcohols or ketones, NMP is also referred to by the chemical names 1-methyl-2-pyrrolidone or N-methyl-2-pyrrolidinone and m-pyrrole, NMP belongs to the class of dipolar aprotic solvents, which also includes dimethylformamide, dimethylacetamide and dimethyl sulfoxide. Due to its good solvency properties, NMP has been used to dissolve a wide range of chemicals, particularly in the polymers field. It also used as a solvent for surface treatment of textiles, resins and metal coated plastics or as a paint stripper.

NMP has been used in the medical industry to improve the solubility of poorly soluble drugs in certain pharmaceutical formulations. For example, NMP has been used with various drugs in veterinary medicine. Several patents have been issued, claiming improvements in drug solubility by the use of NMP, as well as its applicability in topical and transdermal pharmaceutical products for humans.

The relatively non-toxic properties of NMP make it particularly suitable for use as a solvent with the present invention. NMP has a favorable toxicity profile making it a suitable candidate for use in a variety of topical, transdermal and parenteral dosage forms. NMP is available in GMP grade under the trademark Pharmasolve N-methyl-2-pyrrolidone sold by International Specialty Products (ISP; New Jersey, USA).

Dimethyl Sulfoxide (DMSO):

Dimethyl sulfoxide (DMSO) is used in certain embodiments of the present invention as a solvent. DMSO has the formula $(CH_3)_2SO$, DMSO is a polar aprotic solvent that dissolves both polar and non-polar compounds and is miscible in a wide range of organic solvents as well as water.

DMSO is a relatively non-toxic compound, which makes it particularly suitable for use as a solvent within the present invention. The relative lack of toxicity of DMSO is well established, and the potential use of DMSO for medical purposes was established by Stanley Jacob at the University of Oregon Medical School team, who discovered DMSO could penetrate the skin and other membranes without damaging them and could carry other compounds into a biological system. DMSO has also been used as a cryoprotectant and as an anti-inflammatory agent. Dimethyl sulfoxide dissolves a variety of organic substances, including carbohydrates, polymers, peptides, as well as many inorganic salts and gases.

In various embodiments, it is envisioned that lower concentrations, for example, as low as from about 0.1% to about 10%, of DMSO in a composition comprising a volatile anesthetic may be sufficient to eliminate the need for sonication of the composition prior to administration. Higher concentrations, for example, from about 10% to about 75% or higher, of DMSO in a composition comprising a volatile anesthetic may be sufficient to alter the pharmacokinetics of the volatile anesthetic in such a way to allow for an increased rate and/or extent of volatile anesthetic delivered.

Volatile Anesthetics

In general, the halogenated ether anesthetics or volatile anesthetics suitable for use with the described compositions and methods include agents which, although often liquid at room temperature, are capable of easily being becoming gaseous or are already gaseous at room temperature and may reduce inflammation without significant side effects. It may be desirable, for example, to select a volatile anesthetic that is minimally metabolized by the body or is otherwise inert. In this way, liver and kidney toxicity may be minimized. Similarly, it may be desirable for the volatile anesthetic to have a short half-life, or be fast acting to promote titratability (i.e., the subject may easily adjust the delivery amount for the amount of inflammation he or she is experiencing). An active agent gas that does not produce tolerance (unlike opioids or local volatile anesthetics) or dependence (like opioids) may also be desirable.

Volatile anesthetics useful in the compositions and methods of the invention include halogenated ether compounds, isoflurane, sevoflurane, halothane, enflurane, desflurane, methoxyflurane, and diethyl ethers. In certain embodiments xenon may also be used with the present invention. A single agent or mixtures of agents may be particularly suitable for use with the methods described herein.

In various embodiments, a gaseous volatile anesthetic may be used with the present invention. For example, the gaseous volatile anesthetic may be dissolved in a solution according to the present invention and administered in a regional or local procedure, such as transdermally, topically, mucosally, buccally, rectally, orally, intra-articularly, or vaginally. Importantly, the gaseous volatile anesthetic is not administrated by inhalation. In one embodiment, the route of administration is intravenous. In another embodiment, the route of administration is not intravenous. Gaseous volatile anesthetics other than halogenated anesthetics are contemplated, and examples include xenon, nitrous oxide, cyclopropane, and ether, all of which may be used, in various embodiments, in racemic mixture form, or in d-isomer or 1-isomer forms. In various embodiments, other biologically active gases (for example, nitric oxide) may be delivered in a solution to a subject according to the present invention.

More than one volatile anesthetic may be administered at one time, and different volatile anesthetics may be administered at various times throughout a single treatment cycle. For example, two, three, four or more volatile anesthetics may be simultaneously or repeatedly administered to a subject. When compounds are repeatedly administered to a subject, the duration between administration of compounds may be about 1-60 seconds, 1-60 minutes, 1-24 hours, 1-7 days, 1-6 weeks or more, or any range derivable therein. In some instances, it may be desirable to stage the delivery of volatile anesthetics depending on their physical and physiological properties. In certain clinical scenarios, a shorter acting agent may be desirable to treat acute inflammation, whereas a longer lasting agent may be more suited to chronic inflammation applications.

Antibiotics

Antibiotics useful in the compositions and methods of the invention include known antibiotics, as well as those yet to be discovered, Non-limiting examples include Amikacin, Aminoglycoside, Amoxicillin, Ampicillin, Azithromycin, Bacampicillin, Candicidin, Carbenicillin, Cefaclor, Cefadroxil, Cefamandole, Cefazolin, Cefdinir, Cefditoren, Cefepime, Cefonicid, Cefoperazone, Cefotaxime, Cefotetan, Cefoxitin, Cefpodoxime, Cefprozil, Ceftazidime, Ceftibuten, Ceftizoxime, Ceftriaxone, Cefuroxime, Cephalexin, Cephalosporins, Cephapirin, Cephradine, Ciprofloxacin, Claritromycin, Clindamycin, Clotrimazole, Cloxacillin, Crysticillin, Cuprimyxin, Pentids, Permapen, Pfizerpen, Pfizerpen-AS, Wycillin, Demeclocycline, Dicloxacillin, Dirithromycin, Doxycycline, Enoxacin, Erythromycin, Flucloxacillin, Fluoroquinolone, Gatifloxacin, Gemifloxacin, Gentamicin, Haloprogin, Iodochlorohydroxyquin, Kanamycin, Ketolide, Levofloxacin, Lipopeptides, Lomefloxacin, Macrolides, Metronidazole, Mezlocillin, Minocycline, Moxifloxacin, Nafcillin, Neomycin, Netilmicin, Norfloxacin, Nystatin, Ofloxacin, Oxacillin, Oxytetracycline, Paromomycin, Penicillin G, Penicillin V, Penicillins, Piperacillin, Pivampicillin, Pivmecillinam, Roxithromycin, Sparfloxacin, Streptomycin, Sulfamethizole, Sulfamethoxazole, Sulfisoxazole, Sulfonamides, Telithromycin, Tetracyclines, Ticarcillin, Tobramycin, Tolnaftate, Trimethoprim-Sulfamethoxazole, Trovafloxacin, and Vancomycin.

Emulsions

As would be understood by one skilled in the art, an emulsion consists of a mixture of two or more immiscible liquids (i.e., contains multiple phases) and emulsions are distinct from solutions, which contain one or essentially only one phase. One of the liquids (the dispersed phase) is dispersed in the other (the continuous phase). In one type of emulsion, a continuous liquid phase surrounds droplets of water (for example, a water-in-oil emulsion). In another type of emulsion, oil is dispersed within a continuous water phase (for example, an oil-in-water emulsion). Similarly, emulsification is the process by which emulsions are prepared.

In certain embodiments, a volatile anesthetic of the present invention is a component of an emulsion, such as a water-in-oil or an oil-in-water emulsion, including, but not limited to a lipid emulsion, such as a soybean oil emulsion. For example, an volatile anesthetic composition comprising a volatile anesthetic dissolved in a solution comprising an extractive solvent may also comprise a lipid emulsion or an oil-in-water emulsion. In various embodiments, the emulsion of the invention may contain an aqueous solution comprising a volatile anesthetic dissolved in a solution, which may further comprise an extractive solvent. Inclusion of a water-in-oil or an oil-in-water emulsion, such as, for example, a lipid emulsion, in an volatile anesthetic composition may be used, for example, to favorably affect the stability of the volatile anesthetic composition and/or alter the pharmacokinetics of the anesthetic. For example, lipid compositions, lipid emulsions, water-in-oil emulsions, and/or oil-in-water emulsions may be useful for the transdermal, topical, mucosal, buccal, rectal, oral, intra-articular or vaginal delivery of the volatile anesthetic compositions of the present invention. Certain emulsions of isoflurane have been prepared previously for intravenous (da Silva Telles et al., 2004, Rev. Bras. Anaestesiol Campianas 54(5):2004) or epidural administration (Chai et al., 2008, British J Anesthesia 100:109-115; Chai et al., 2006, Anesthesiology 105: A743), both for inducing anesthesia.

In certain embodiments, the emulsion of the invention comprises a volatile anesthetic and water, and may further comprise an emulsifier. Emulsions of the invention also include, but are not limited to, nanoemulsions, which are emulsions with a mean droplet size less than those of emulsions. Nanoemulsions are sometimes referred to as microemulsions and submicroemulsions. Often, the physical appearance of a nanoemulsion is transparent, rather than the often milky appearance of an emulsion, due to the reduced mean droplet size. Emulsions of the invention also include, but are not limited to, liquid crystal emulsions, such as those disclosed, for example, in U.S. Patent Application Nos. 20070149624 and 20050238677, U.S. Pat. No. 5,183,585 and International Patent Application No. WO 05108383.

In certain embodiments, the emulsion of the invention may have a lipid component. In various embodiments, the lipid component may comprise an amount ranging from about 1% to 99%, from about 5% to about 75%, from about 10% to about 60%, from about 20% to about 50%, or from about 30% to about 40%, v/v of the emulsion. In various embodiments, the lipid component of the emulsion may be soybean oil, long chain triglyceride, castor oil, corn oil, cottonseed oil, olive oil, peanut oil, peppermint oil, safflower oil, sesame oil, soybean oil, hydrogenated soybean oil, hydrogenated vegetable oil, medium chain triglycerides coconut oil, palm see oil and derivatives, medium chain (C8/C10) mono- and diglycerides, d-alpha-tocopherol, soy fatty acids, or combinations thereof. In certain embodiments, the lipid component of the emulsion is soybean oil. Commercially available lipid compositions that may be useful for the production of the volatile anesthetic compositions of the present invention include, but are not limited to, Intralipid®, Liposyn®, and Nutrilipid®.

In other embodiments, the emulsion further comprises an emulsifier. An emulsifier is a substance that stabilizes an emulsion. An emulsifier may also known as an emulgent. An emulsifier may also be a surfactant. In various embodiments, the emulsifier may be egg phospholipid, purified egg phospholipids, Polyoxyl 35 castor oil (Cremophor EL), Polyoxyl 40 hydrogenated castor oil (Cremophor RH 40), Polyoxyl 60 hydrogenated castor oil (Cremophor RH 60), Polysorbate 20, Polysorbate 80, d-alpha-tocopheryl polyethylene glycol 1000 succinate, Solutol HS-15, propylene glycol, or combinations thereof. Various concentrations of an emulsifier may be used with the present invention. For example, a composition of the present invention comprising a volatile anesthetic may comprise about 0.1%-99%, 0.1%-60%, 5%-50%, 10%-40%, 5%-25%, 10%-30%, 10%-25%, 25%-

50%, 10%-75%, 25%-75%, 10%-65%, 25%-65%, 10%-60%, 25%-60%, 0.1%, 1%, 5%, 10%, 20%, 25%, 30%, 35%, 40%, 45%, 50%, 55%, 60%, 65%, 70%, 75%, 80% or any range derivable therein, of an emulsifier.

In other embodiments, the emulsion of the invention has a perfluorocarbon component. In various embodiments, the perfluorocarbon component may comprise an amount ranging from about 0.1% to 99%, from about 5% to about 75%, from about 10% to about 60%, from about 20% to about 50%, or from about 30% to about 40%, v/v of the emulsion. In various embodiments, perfluorocarbon may provide additional advantages due to its limited toxicity and ability to scavenge a large amount of gas. In one embodiment, the emulsion of the invention comprises a volatile anesthetic, a perfluorocarbon, water and an emulsifier. A perfluorocarbon, specifically perfluoro-n-octane, has been used clinically, in cases of retinal detachment, by its instillation into the eye in place of the aqueous humor (see Chang, 1992, S. Intl. Ophthalmol. Clinic 32:153-163).

Liposomes and Micro-Droplets

In various embodiments, the volatile anesthetics of the present invention may be a component of a liposome suspension. A liposome (for example, multilamellar, unilamellar, and/or multivesicular liposomes) is a microscopic, spherical, fluid-filled structure, with walls comprising one or more layers of phospholipids and molecules similar in physical and/or chemical properties to those that make up mammalian cell membranes. By way of nonlimiting examples, liposomes may be formed from a variety of natural membrane components, such as cholesterol, stearylanine, or phosphatidylcholine (see, for example, U.S. Pat. Nos. 5,120,561 and 6,007,838, each of which is incorporated herein by reference in its entirety), or of pure surfactant components like DOPE (dioleoylphosphatidyl-ethanolamine). Liposomes may be formulated to incorporate a wide range of materials as a payload either in the aqueous or in the lipid compartments or in both. Generally, lipophilic active substances dissolve in the bilayer, amphiphilic substances become associated with the phospholipid membrane and hydrophilic substances occur in solution in the enclosed aqueous volume (Artmann et al., 1990, Drug Res. 40 (11) 12:1363-1365; incorporated herein by reference in its entirety).

Liposomes useful as drug carriers or for topical use that are non-toxic and available in industry (Gehring et al., 1990, Drug Res. 40 (11) 12:1368-1371; incorporated herein by reference in its entirety), Liposomes have been used as carriers for lipophilic drugs like the anti-tumor and the anti-viral derivatives of azidothymidine (AZT) (Kamps, et al., 1996, Biochim. Biophys. Acta. 1278:183-190). Insulin has also been delivered via liposomes (Muramatsu et al., 1999, Drug Dev. Ind. Pharm. 25:1099-1105). For medical uses as drug carriers, the liposomes may also be injected, and when they are modified with lipids, their surfaces become more hydrophilic and hence their ability to persist may be increased. Polyethylene glycol-modified liposomes have been used as carriers for hydrophilic (water-soluble) anti-cancer drugs like doxorubicin. Liposomal derivatives of mitoxantrone and others are especially effective in treating diseases that affect the phagocytes of the immune system because they tend to accumulate in the phagocytes, which recognize them as foreign invaders (Rentsch et al., 1997, Br. J. Cancer 75:986-992). Liposomes have also been used to carry normal genes into a cell to treat diseases caused by defective genes (Guo et al., 2000, Biosci. Rep. 20:419-432). The versatility of liposomes, due to the variable composition, enables liposomes to be used to deliver vaccines, proteins, nucleotides, plasmids, drugs, cosmetics, or the volatile anesthetics of the invention to the body.

Liposome compositions of the invention may comprise any range of liposome and volatile anesthetic components, according to the methods and detailed description set forth herein. By way of a non-limiting example, a liposome component of a composition of the invention may include from 0.1% to 99.9% liposome component, or more preferably, from 0.1%-50% liposome component, and even more preferably, from 0.1%-30% liposome component. In various embodiments, the liposome of the invention comprises cholesterol, stearylamine, phosphatidylcholine, dioleoyl-phosphatidylethanolamine, or combinations thereof.

In various embodiments, the volatile anesthetics of the present invention may also be a component of a microdroplet. A micro-droplet of the invention consists of a sphere of organic liquid phase drug that ranges in diameter from about 200 Angstroms to about 10,000 Angstroms that is covered by a monolayer of a suitable lipid. Preferred lipids are phospholipids, which are natural constituents of biological membranes and as such are biologically compatible. Compounds useful for preparing microdroplets include phosphatidylcholine (lecithin), sphingomyelin, phosphatidic acid, phosphatidyl serine, phosphatidyl inositol, diphosphatidyl glycerol and phosphatidyl glycerol.

Micro-droplets may be prepared by sonication, including probe or bath sonication, homogenization, microfluidization or by high intensity mechanical agitation. The preferred method of preparing the microdroplets of the invention is by sonication with a probe sonicator. Alternatively, microdroplets may be prepared in a bath sonicator. For small scale preparations a 1.0 cm diameter test tube is suspended, with use of a test-tube clamp, in a bath sonicator filled with water. The components of the microdroplet are first grossly mixed by shaking, Vortex mixing, Polytron or other methods. The suspension is then introduced into the bath sonicator and sonicated for 1-2 hours. If the preparation is to be done on a large scale, it is possible to omit the test tube and introduce the components of the microdroplet directly into a bath sonicator. Micro-droplets may also be produced by high intensity mechanical agitation. Useful methods include a Waring blender, a Polytron and high frequency shakers such as a commercial paint shaker. Other materials and methods useful in the preparation of microdroplets are known in the art and are described in U.S. Pat. Nos. 4,622,219, 4,725,442, and 5,091,188, Haynes et al. (1989, J. Contr. Rel, 9:1-12) and Haynes et al. (1985, Anesthesiology 63:490-499), all of which references are incorporated herein in their entirety.

Dosing

The amount of the volatile anesthetic to be administered depends on the particular indication desired. For example, the dose will depend on the type of inflammation intended to be treated. The dose may be different, for instance, if the delivery of the volatile anesthetic is intended to reduce chronic inflammation as opposed to acute inflammation. Similarly, the dose may be different if the volatile anesthetic composition is used to anesthetize a subject (generally or locally, including topically, mucosally, buccally, orally, intra-articularly, rectally or vaginally). The subject's physical characteristics may also be important in determining the appropriate dosage. Characteristics such as weight, age, and the like may be important factors. For example, the volatile anesthetic may have increased potency with age, as has been demonstrated in the case of the volatile anesthetic isoflurane.

The temperature of the volatile anesthetic may also be considered as a factor in selecting an appropriate dose, as the solubility of many volatile anesthetics may be affected by the temperature of the volatile anesthetic and/or solution. For example, increases in temperature may increase the solubility, and thus potency, of the volatile anesthetic composition; this property has been demonstrated with certain volatile anesthetics. The particular dosage may also be dependent on the dosing regime chosen. For example, the volatile anesthetic composition may be delivered continuously or periodically. Conversely, the volatile anesthetic composition may be administered as a single administration as a one-time event.

Volatile anesthetics (for example, halogenated volatile anesthetic compounds) may be applied in amounts leading to concentrations in the range of about 250 to about 50,000 nanograms/cm$^2$ of target site of action, depending on the volatile anesthetic selected and the desired effect. In certain embodiments, a halogenated volatile anesthetic or volatile anesthetic may be administered to achieve a concentration of from about 5 to about 5,000,000 nanograms/cm$^2$ of target site of action. While the dose range will vary depending on the compound selected and patient variability, it is generally true that lower doses such as from about 0.01 to about 10,000 nanogram/cm$^2$ of target site of action are more suitable for treating minor to moderate inflammation, while higher doses such as from about 10,000 nanogram/cm$^2$ of target site of action to about 500,000 nanogram/cm$^2$ of target site of action or more are suitable for treating severe inflammation. Of course, the doses may be given once (for example, for a minor single occurrence of inflammation), repeatedly (for example, for moderate or chronic inflammation), or continuously (for example, for severe inflammation). Combinations of these dosing regimes may also be used. For example, a subject suffering from severe inflammation may require continuous dosing with periodic additional dosing.

In embodiments where an volatile anesthetic (for example, a volatile anesthetic, isoflurane, etc.) is mixed in a solution, such as water, saline or an artificial CSF solution, the concentration of the volatile anesthetic may vary. For example, a solution may contain volatile anesthetic in a v/v ratio of from about 1 to about 99%, from about 10 to about 75%, from about 10 to about 50%, from about 20 to about 50%, from about 30 to about 50%, from about 1 to about 45%, from about 1 to about 40%, from about 1 to about 35%, from about 1 to about 30%, from about 1 to about 25%, from about 1 to about 20%, from about 1 to about 15%, from about 1 to about 10%, from about 1 to about 5%, from about 0.5 to about 5%, from about 0.1 to about 5%, from about 0.1 to about 2.5%, from about 0.5 to about 2.5%, or any range derivable therein. In these embodiments, the volatile anesthetic may be a volatile anesthetic, for example, isoflurane, and the solution may be water, a saline solution, artificial cerebrospinal fluid (ACSF), or other fluid.

The dosing and manner of delivery of the compositions of the invention may be adjusted to achieve inflammation reduction, for example, by varying the amount, concentration, frequency of administration, and timing of administration.

The volatile anesthetic solution may also contain one or more additives, such as a surfactant, PVP, a polymers, an antimicrobial agent, a preservative etc. In certain embodiments, an volatile anesthetic composition of the present invention may comprise about: 0.1-90% of a volatile anesthetic such as isoflurane, methoxyflurane, or sevoflurane, 0.1-99% of an extractive solvent such as NMP or DMSO, 0.1-99% saline, and 0-50% other additive(s) (for example, glycerol, a surfactant, PVP, etc.). In some embodiments, it may be desirable to produce a concentrated formulation which may be subject to a final dilution prior to administration.

In various embodiments, a solution of about 10% volatile anesthetic, such as isoflurane, may be used; this solution may be administered as a one-time, continuously, and/or repeatedly to achieve wound treatment and/or a diminution in the level of inflammation. A further aspect of the compositions and methods of the invention for the treatment of wounds and inflammation is the analgesic activity of the volatile anesthetics. Thus, a 10% v/v solution of a volatile anesthetic may be used to treat wounds. Higher concentrations and/or longer durations of volatile anesthetic may be used, in various embodiments, as necessary.

Methods of Active Agent Delivery

Volatile anesthetics of the present invention may be delivered topically. In some embodiments, specific concentrations of volatile anesthetics which may be used for topical delivery include from about 100 to about 500,000 nanogram/cm$^2$ of target site of action, from about 100 to about 250,000 nanogram/cm$^2$ of target site of action, from about 100 to about 100,000 nanogram/cm$^2$ of target site of action, from about 100 to about 50,000 nanogram/cm$^2$ of target site of action, from about 100 to about 25,000 nanogram/cm$^2$ of target site of action, or from about 100 to about 10,000 nanogram/cm$^2$ of target site of action. The specific concentration of volatile anesthetic used may vary depending on the desired effect, and in various embodiments the volatile anesthetic composition is titrated for effect: thus the concentration of volatile anesthetic used or achieved in tissues may vary depending on the specific desired result and/or the particular characteristics of the patient such as sensitivity to the volatile anesthetic.

In certain embodiments, compositions and methods of the present invention may be used to diminish inflammation. In some embodiments, specific concentrations of volatile anesthetics which may be used to reduce inflammation include from about 100 to about 500,000 nanogram/cm$^2$ of target site of action, from about 100 to about 250,000 nanogram/cm$^2$ of target site of action, from about 100 to about 100,000 nanogram/cm$^2$ of target site of action, from about 100 to about 50,000 nanogram/cm$^2$ of target site of action, from about 100 to about 25,000 nanogram/cm$^2$ of target site of action, or from about 100 to about 10,000 nanogram/cm$^2$ of target site of action.

The pharmaceutical compositions of the invention may be dispensed to the subject under treatment with the help of an applicator. The applicator to be used may depend on the specific medical condition being treated, amount and physical status of the pharmaceutical composition, and choice of those skilled in the art.

The pharmaceutical compositions of the invention may be provided to the subject or the medical professional in charge of dispensing the composition to the subject, along with instructional material. The instructional material includes a publication, a recording, a diagram, or any other medium of expression, which may be used to communicate the usefulness of the composition and/or compound used in the practice of the invention in a kit. The instructional material of the kit may, for example, be affixed to a container that contains the compound and/or composition used in the practice of the invention or shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

Other routes of administration to the affected area which are contemplated include: injection, infusion, continuous infusion, localized perfusion bathing target cells directly, via a catheter, via nanoparticle delivery, intravenous, intramuscular, cutaneous, subcutaneous, transdermal, or topical administration (for example, in a carrier vehicle, a topical control release patch, in a wound dressing, a hydrocolloid, a foam, or a hydrogel, a cream, a gel, a lotion, an ointment, a liquid crystal emulsion (LCE), and/or a micro-emulsion). An appropriate biological carrier or pharmaceutically acceptable excipient may be used. Compounds administered may, in various embodiments, be racemic, isomerically purified, or isomerically pure.

Oral Administration.

A formulation of a pharmaceutical composition used in the practice of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion. As used herein, an "oily" liquid comprises a carbon-containing liquid molecule that exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture.

Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition used in the practice of the invention that are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropyl methylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Powdered and granular formulations of a pharmaceutical preparation used in the practice of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition used in the practice of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (e.g. such as with a physiologically degradable material), and methods of absorbing an aqueous or oily solution or suspension into an absorbent material, with or without subsequent drying.

Parenteral Administration.

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents, may be used.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules, crushable or otherwise, or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (e.g. powder or granular) form for reconstitution with a suitable vehicle (e.g. sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non toxic parenterally acceptable diluent or solvent, such as water or 1,3-butanediol, for example. Other acceptable diluents and solvents include, but are not limited to, Ringer's solution, isotonic sodium chloride solution, and fixed oils such as synthetic mono- or diglycerides. Other usual parentally-administrable formulations include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Transmucosal Administration.

Transmucosal administration is carried out using any type of formulation or dosage unit suitable for application to mucosal tissue. For example, the selected active agent may be administered to the buccal mucosa in an adhesive tablet or patch, sublingually administered by placing a solid dosage form under the tongue, lingually administered by placing a solid dosage form on the tongue, administered nasally as droplets or a nasal spray, a non-aerosol liquid formulation, or a dry powder, placed within or near the rectum ("transrectal" formulations), or administered to the urethra as a suppository, ointment, or the like.

Transurethal Administration.

With regard to transurethal administration, the formulation may comprise a urethral dosage form containing the active agent and one or more selected carriers or excipients, such as water, silicone, waxes, petroleum jelly, polyethylene glycol ("PEG"), propylene glycol ("PG"), liposomes, sugars such as mannitol and lactose, and/or a variety of other materials. A transurethral permeation enhancer may be included in the dosage from. Examples of suitable permeation enhancers include dimethylsulfoxide ("DMSO"), dimethyl formamide ("DMF"), N,N-dimethylacetamide ("DMA"), decylmethylsulfoxide ("C10 MSO"), polyethylene glycol monolaurate ("PEGML"), glycerol monolaurate, lecithin, the 1-substituted azacycloheptan-2-ones, particularly 1-n-dodecyl-cyclazacycloheptan-2-one (available under the trademark Azone™ from Nelson Research & Development Co., Irvine, Calif.), SEPA™ (available from Macrochem Co., Lexington, Mass.), surfactants as discussed above, including, for example, Tergitol™, Nonoxynol-9™ and TWEEN-80™, and lower alkanols such as ethanol.

Transrectal Administration.

Transrectal dosage forms may include rectal suppositories, creams, ointments, and liquid formulations (enemas). The suppository, cream, ointment or liquid formulation for transrectal delivery comprises a therapeutically effective amount of the selected active agent and one or more conventional nontoxic carriers suitable for transrectal drug administration. The transrectal dosage forms of the present invention may be manufactured using conventional processes. The transrectal dosage unit may be fabricated to disintegrate rapidly or over a period of several hours. The time period for complete disintegration may be in the range of from about 10 minutes to about 6 hours, e.g., less than about 3 hours.

Vaginal or Perivaginal Administration.

Vaginal or perivaginal dosage forms may include vaginal suppositories, creams, ointments, liquid formulations, pessaries, tampons, gels, pastes, foams or sprays. The suppository, cream, ointment, liquid formulation, pessary, tampon, gel, paste, foam or spray for vaginal or perivaginal delivery comprises a therapeutically effective amount of the selected active agent and one or more conventional nontoxic carriers suitable for vaginal or perivaginal drug administration. The vaginal or perivaginal forms of the present invention may be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and 6,086,909). The vaginal or perivaginal dosage unit may be fabricated to disintegrate rapidly or over a period of several hours. The time period for complete disintegration may be in the range of from about 10 minutes to about 6 hours, e.g., less than about 3 hours.
Topical Formulations.

Topical formulations may be in any form suitable for application to the body surface, and may comprise, for example, an ointment, cream, gel, lotion, solution, paste or the like, and/or may be prepared so as to contain liposomes, micelles, and/or microspheres. In certain embodiments, topical formulations herein are ointments, creams and gels.
Transdermal Administration.

Transdermal compound administration, which is known to one skilled in the art, involves the delivery of pharmaceutical compounds via percutaneous passage of the compound into the systemic circulation of the patient. Topical administration may also involve the use of transdermal administration such as transdermal patches or iontophoresis devices. Other components may be incorporated into the transdermal patches as well. For example, compositions and/or transdermal patches may be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions may include creams, sprays, lotions, gels, ointments, eye drops, nose drops, ear drops, and the like. In such dosage forms, the compositions of the invention may be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions may contain polyethylene glycol 400. They may be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, may be impregnated with the compositions in solution, lotion, cream, ointment or other such form may also be used for topical application. The compositions may also be applied topically using a transdermal system, such as one of an acrylic-based polymer adhesive with a resinous cross-linking agent impregnated with the composition and laminated to an impermeable backing.

Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are separate and distinct layers, with the adhesive underlying the reservoir that, in this case, may be either a polymeric matrix as described above, or be a liquid or hydrogel reservoir, or take some other form.
Intrathecal Administration.

One common system utilized for intrathecal administration is the APT Intrathecal treatment system available from Medtronic, Inc. APT Intrathecal uses a small pump that is surgically placed under the skin of the abdomen to deliver medication directly into the intrathecal space. The medication is delivered through a small tube called a catheter that is also surgically placed. The medication may then be administered directly to cells in the spinal cord involved in conveying sensory and motor signals associated with lower urinary tract disorders.
Intravesical Administration.

The term intravesical administration is used herein in its conventional sense to mean delivery of a drug directly into the bladder. Suitable methods for intravesical administration may be found, for example, in U.S. Pat. Nos. 6,207,180 and 6,039,967.
Additional Administration Forms.

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Application Nos. 20030147952, 20030104062, 20030104053, 20030044466, 20030039688, and 20020051820, Additional dosage forms of this invention also include dosage forms as described in PCT Application Nos, WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.
Solutions After a halogenated ether volatile anesthetic has been selected, it may be dissolved into a solution. The solution may be an aqueous-based solution, such as water, saline, or the like. In some variations, other fluids and solutions may be appropriate.

Various formulations of saline are known in the art and may be used with the present invention. For example, the saline may be lactated Ringer's solution, acetated Ringer's solution, phosphate buffered saline (PBS), Dulbecco's phosphate buffered saline (D-PBS), Tris-buffered saline (TBS), Hank's balanced salt solution (HBSS), or Standard saline citrate (SSC).

The saline solutions of the present invention are, in certain embodiments, "normal saline" (i.e., a solution of about 0.9% w/v of NaCl). Normal saline has a slightly higher degree of osmolality compared to blood; however, in various embodiments, the saline may be isotonic in the body of a subject such as a human patient. Normal saline (NS) is often used frequently in intravenous drips (IVs) for patients who cannot take fluids orally and have developed severe dehydration. In certain embodiments, "half-normal saline" (i.e., about 0.45% NaCl) or "quarter-normal saline" (i.e., about 0.22% NaCl) may be used with the present invention. Optionally, about 5% dextrose or about 4.5 g/dL of glucose may be included in the saline. In various embodiments, one or more salt, buffer, amino acid and/or antimicrobial agent may be included in the saline.

In various embodiments, a preservative or stabilizer may be included in the composition or solution. For example, the prevention of the action of microorganisms may be brought about by preservatives such as various antibacterial and antifungal agents, including but not limited to parabens (for example, methylparabens, propylparabens), chlorobutanol, phenol, sorbic acid, EDTA, metabisulfite, benzyl alcohol, thimerosal or combinations thereof. Agents that may be included suitable for use include sterile aqueous solutions or dispersions and sterile powders for the extemporaneous preparation of sterile solutions or dispersions (U.S. Pat. No. 5,466,468, specifically incorporated herein by reference in its entirety). In all cases the composition is preferably sterile and must be fluid to facilitate easy injectability. Solutions are preferably stable under the conditions of manufacture and storage and must be preserved against the contaminating action of microorganisms, such as bacteria and fungi. Examples of stabilizers which may be included include buffers, amino acids such as glycine and lysine, carbohydrates such as dextrose, mannose, galactose, fructose, lactose, sucrose, maltose, sorbitol, mannitol, and the like. Appropriate stabilizers or preservatives may be selected according to the route of administration desired. A particle filter or microbe filter may be used, and may be necessary according to the route of administration desired.

The weight ranges of compounds in the solution may vary. For example, in various embodiments, the composition may comprise about 1-5 wt % volatile anesthetic, about 1-5 wt % preservative/stabilizer, about 1-5 wt % NaCl, and about 85%-97% water. The ratio of volatile anesthetic to water may be varied as needed to achieve the desired reduction of inflammation.

The solution and/or composition may also be sterilized prior to administration. Methods for sterilization are well known in the art and include heating, boiling, pressurizing, filtering, exposure to a sanitizing chemical (for example, chlorination followed by dechlorination or removal of chlorine from solution), aeration, autoclaving, and the like.

The active agent gas may be formulated into a solution in any number of ways. For example, it may be bubbled through the solution, for example, using a vaporizer, or it may be solubilized by agitation or by sonication. In certain embodiments, a volatile anesthetic such as a halogenated ether or a volatile anesthetic may be measured in liquid form and directly admixed into a solution. Of course, other suitable methods of dissolving the volatile anesthetic into solution may also be used. After the halogenated ether volatile anesthetic has been solubilized, it may be administered to a subject in need of reduction of inflammation. In certain embodiments, a volatile anesthetic is admixed with a solution in a closed vacuum container, and the combined solutions are then mechanically agitated for 3-5 minutes and held in a thermo-neutral sonicator until use.

In certain embodiments, solutions of the present invention may be a component of an emulsion, such as a water-in-oil or an oil-in-water emulsion, including a lipid emulsion, such as a soybean oil emulsion. In certain embodiments, saline, artificial CSF, or the patients own CSF, alone or as a constituent of an emulsion, may be used for intrathecal or epidural administration of an volatile anesthetic according to the present invention. Certain emulsions of isoflurane have been prepared previously for intravenous (da Silvaa Telles, et al., 2004, Rev. Bras. Anaestesiol Campianas 54(5):2004) or epidural administration (Chai et al. 2008, British J Anesthesia 100:109-115).

Pharmaceutical compositions of the present invention comprise an effective amount of one or more volatile anesthetics or biologically active gas or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one volatile anesthetic or biologically active gas in solution or additional active ingredient will be known to those of skill in the art in light of the present disclosure, as exemplified by "Remington: The Science and Practice of Pharmacy," 20th Edition (2000), which is incorporated herein by reference in its entirety. Moreover, for animal (for example, human) administration, it will be understood that preparations should meet sterility, pyrogenicity, general safety and purity standards as required by FDA Office of Biological Standards.

In various embodiments, the compositions of the present invention further comprise cyclodextrin. Cyclodextrins are a general class of molecules composed of glucose units connected to form a series of oligosaccaride rings (See Challa et al., 2005, AAPS PhannSciTech 6:E329-E357). In nature, the enzymatic digestion of starch by cyclodextrin glycosyltransferase (CGTase) produces a mixture of cyclodextrins comprised of 6, 7 and 8 anhydroglucose units in the ring structure ($\alpha$-, $\beta$-, and $\gamma$-cyclodextrin, respectively). Commercially, cyclodextrins are also produced from starch, but different, more specific enzymes are used. Cyclodextrins have been employed in formulations to facilitate the delivery of cisapride, chloramphenicol, dexamethasone, dextromethoraphan, diphenhydramine, hydrocortisone, itraconazole, and nitroglycerin (Welliver and McDonough, 2007, Sci World J, 7:364-371). In various embodiments, the cyclodextrin of the invention is hydroxypropyl-Beta-cyclodextrin, sulfobutylether-beta-cyclodextrin, alpha-dextrin or combinations thereof. In certain embodiments, cyclodextrin may be used as a solubilizing agent.

In various other embodiments, compositions of the present invention may comprise human serum albumin purified from plasma, or recombinant human serum albumin. In certain embodiments, human serum albumin may be used as a solubilizing agent. In other embodiments, the compositions of the invention may comprise propylene glycol. In other embodiments, the compositions of the invention may comprise perfluorooctyl bromide. In other embodiments, the compositions of the invention may comprise perfluorocarbon. In certain embodiments, perfluorocarbon may be used as a soliabilizing agent.

In various embodiments, a preservative or stabilizer may be included in the composition or solution. For example, the prevention of the action of microorganisms may be brought about by preservatives such as various antibacterial and antifungal agents, including but not limited to parabens (for example, methylparabens, propylparabens), chlorobutanol, phenol, sorbic acid, EDTA, metabisulfite, benzyl alcohol, thimerosal or combinations thereof. Agents which may be included suitable for use include sterile aqueous solutions or dispersions and sterile powders for the extemporaneous preparation of sterile solutions or dispersions (U.S. Pat. No. 5,466,468, specifically incorporated herein by reference in its entirety). In all cases the composition is preferably sterile and must be fluid to facilitate easy injectability. Solutions are preferably stable under the conditions of manufacture and storage and must be preserved against the contaminating action of microorganisms, such as bacteria and fungi. Examples of stabilizers which may be included include buffers, amino acids such as glycine and lysine, carbohydrates such as dextrose, mannose, galactose, fructose, lactose, sucrose, maltose, sorbitol, mannitol, etc. Appropriate stabilizers or preservatives may be selected according to the route of administration desired. A particle filter or microbe filter may be used and may be necessary according to the route of administration desired.

Pharmaceutical Compositions and Therapies

Administration of compositions of the invention in a method of treatment may be achieved in a number of different ways, using methods known in the art. Such methods include, but are not limited to, topically administering solutions, suspensions, creams, pastes, oils, lotions, gels, foam, hydrogel, ointment, liposomes, emulsions, liquid crystal emulsions, and nanoemulsions.

The therapeutic and prophylactic methods of the invention thus encompass the use of pharmaceutical compositions of the invention. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit. For example unit dose container may be such that volatile anesthetic solution is contained in a crushable sealed ampoule which in turn is enclosed in protective covering on which pressure is applied to crush the ampoule which then releases volatile anesthetic solution for percolation through a flint-type tip which capped the ampoule in protective covering. When such packaging configuration is employed, care is taken to leave as little as possible or ideally no headspace in ampoule for the volatile anesthetic to escape and cause a change in solution composition over a period of shelf life.

Although the description of pharmaceutical compositions provided herein are principally directed to pharmaceutical compositions which are suitable for ethical administration to humans, it will be understood by the skilled artisan that such compositions are generally suitable for administration to animals of all sorts, including mammals. Modification of pharmaceutical compositions suitable for administration to humans in order to render the compositions suitable for administration to various animals is well understood, and the ordinarily skilled veterinary pharmacologist may design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, intra-articular, vaginal, topical, intranasal, buccal, intravenous, intramuscular, or another route of administration.

A pharmaceutical composition of the invention may be prepared, packaged, or sold in bulk, as a single unit dose, or as a plurality of single unit doses. A unit dose is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. One non-limiting example of such an additional pharmaceutically active agent is an antimicrobial agent, such as an antibiotic.

Controlled- or sustained-release formulations of a pharmaceutical composition of the invention may be made using conventional technology.

Formulations of a pharmaceutical composition suitable for topical administration comprise the active ingredient combined with a pharmaceutically acceptable carrier, such as sterile water or sterile isotonic saline. Such formulations may be prepared, packaged, or sold in a form suitable for bolus administration or for continuous administration. Formulations may be prepared, packaged, or sold in unit dosage form, such as in ampules, crushable or otherwise, or in multi-dose containers containing a preservative. Formulations for topical administration include, but are not limited to, suspensions, solutions, emulsions in oily or aqueous vehicles, solutions, suspensions, creams, pastes, oils, lotions, gels, foam, hydrogel, ointment, liposomes, emulsions, liquid crystal emulsions, nanoemulsions, implantable sustained-release or biodegradable formulations. Such formulations may further comprise one or more additional ingredients including, but not limited to, suspending, stabilizing, or dispersing agents.

The pharmaceutical compositions may be prepared, packaged, or sold in the form of a sterile aqueous or oily suspension or solution. This suspension or solution may be formulated according to the known art, and may comprise, in addition to the active ingredient, additional ingredients such as the dispersing agents, wetting agents, or suspending agents described herein. Such sterile formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other formulations which are useful include those which comprise the active ingredient in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

In some embodiments, the pharmaceutical compositions of the invention may be contained in a crushable ampule irrespective of the route of delivery to the patient.

DEFINITIONS

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well known and commonly employed in the art.

The articles "a" and "an" are used herein to refer to one or to more than one (i.e. to at least one) of the grammatical object of the article. By way of example, "an element" means one element or more than one element.

Throughout this application, the term "about" is used to indicate that a value includes the inherent variation of error for the device, the method being employed to determine the value, or the variation that exists among the study subjects.

The term "or," as used herein, means "and/or" unless explicitly indicated to refer to alternatives only or the alternatives are mutually exclusive, although the disclosure supports a definition that refers to only alternatives and "and/or."

The terms "inhibiting," "reducing," or "preventing," "diminishing," and variations of these terms, as used herein include any measurable decrease, including complete or substantially complete inhibition.

The term "effective," as that term is used in the specification and/or claims, means adequate to accomplish a desired, expected, or intended result.

The phrase "extractive solvent," as used herein, refers to a solvent which may interact with a volatile anesthetic in solution to reduce the volatility of the volatile anesthetic without chemically reacting to the volatile anesthetic, and/or enhances permeability of volatile anesthetic into the tissue of interest, favoring either achievement or enhancement of an intended pharmacological outcome. Extractive solvents also comprise compounds that do not necessarily extract, including vehicles and functional components, that may affect properties such as, but not limited to, permeability or penetration.

As used herein, the term "enhanced permeability" refers to increase in (a) amount of volatile anesthetic delivered to the tissue of interest and/or (b) rate of delivery (i.e., rapid delivery) to the tissue of interest and/or (c) residence time of volatile anesthetic in the tissue of interest. Increase in residence time refers to a delay in elimination of volatile anesthetic from tissue of interest.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the term "wound" is used to mean an area, a region or a site on the surface of, or inside the body of, a subject that exhibits a tissue injury. The wound that may be treated using the composition and methods of the invention includes any wound, including those caused by surgery and those caused by trauma. Wounds that may be treated by the compositions and methods of the invention, include, but are not limited to, a lesion, an abscess, an incision, a laceration, an abrasion, a puncture, a penetration, a burn or other type of tissue injury. The wound that may be treated using the compositions and methods of the invention includes any wound on the surface of, or inside the body of, a patient that may be exposed to the compositions and methods of the invention. By way of nonlimiting examples, areas, regions and sites that may be treated by the methods of the invention include, but are not limited to, external tissues (e.g. skin, mucosa etc.), internal tissues (e.g. muscle, mucosa, fascia, adipose tissue, tendons, and connective tissues etc.), and internal organs (e.g. lungs, liver, etc.). It should be understood that many areas, regions and sites that may not normally be amenable to exposure to the compositions and methods of the invention, may become amenable to exposure to the compositions and methods of the invention, after a wound, such as, for example, a surgical incision or traumatic laceration, is introduced to the body of a subject. By way of nonlimiting examples, such an area, region or site may include a trauma wound, a surgical wound, and a burn.

The term "topical," as used herein, refers to the administration of the compositions of the invention to the skin and underlying tissues, as well as to administration to the mucosa and underlying tissues.

The term "treat" or "treatment," as used herein, refers to the alleviation (i.e., "diminution") and/or the elimination of a sign/symptom or a source of a sign/symptom. By way of several non-limiting examples, a wound may be treated by alleviating a sign/symptom of a wound (e.g., inflammation). A sign/symptom of a wound may also be treated by altogether eliminating a sign/symptom of the wound (e.g. inflammation). By way of a further example, a wound may be treated by aiding (e.g., accelerating) the healing process.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents; demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

Throughout this disclosure, various aspects of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual and partial numbers within that range, for example, 1, 2, 3, 4, 5, 5.5 and 6. This applies regardless of the breadth of the range.

It is contemplated that any embodiment discussed in this specification may be implemented with respect to any method or composition of the invention, and vice versa. Furthermore, compositions of the invention may be used to achieve methods of the invention.

Other objects, features and advantages of the present invention will become apparent from the detailed description herein. It should be understood, however, that the detailed description and the specific examples, while indicating specific embodiments of the invention, are given by way of illustration only, since various changes and modifications within the spirit and scope of the invention will become apparent to those skilled in the art from this detailed description.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Administration of Isoflurane and Sevoflurane to a Wound

This study is designed to evaluate efficacy of topical application of volatile anesthetics to treat wounds. The study is conducted over a one (1) month to (3) month period using the volatile anesthetics isoflurane and sevoflurane applied directly to the wound using both an Incision Wound Animal model and a Burn Wound Animal Model. The subject animal is the rat.

In the Incision Wound Animal Model, each rat is anesthetized, and two long incisions are made on the back of the rat. The incisions are then sutured. In the Burn Wound Animal Model, each rat is anesthetized, and two burns are made on the back of the rat. On each rat, one of the wounds is treated using the compositions and methods of the invention described elsewhere herein, and the other wound is left untreated.

For each group of 3 cohorts of rats detailed herein, for both the Burn and Incision Models, the extent of inflammation and the progress of wound healing is monitored over a 30-90 day period to assess the efficacy of topical administration of volatile anesthetics in treating wounds and in reducing inflammation. In the first cohort, preservative-free normal saline is used as a mock treatment of the wound. In the second cohort, isoflurane is used to treat the wound. In the third cohort, sevoflurane is used to treat the wound.

Example 2

Preparation of Isoflurane Dissolved in Saline

Isoflurane was dissolved into saline using the following method (also referred to as the "bubbling" method). A mock vaporizing device was created using a 500 ml modified Erlenmeyer flask (2 inlets and 1 catheter into the liquid phase). The flask was partially filled with 0.9% normal saline and a stoppered glass pipette was inserted into the bottom of the liquid phase for injection of isoflurane. A second egress pipette allowed egress of gas from the closed container. 2% isoflurane solution in oxygen at 2 L/min was injected through the pipette, saturating the 0.9% saline solution after approximately 10 minutes of bubbling.

Example 3

Isoflurane Dissolved in Artificial Cerebrospinal Fluid

Isoflurane dissolved in ACSF was prepared by the following method. Isoflurane was mixed in a closed vacuum container in a v/v ratio of 10-50% with buffered salt solution that approximates cerebrospinal fluid (pH 7.4) with the following composition (in mM): NaCl, 120; KC, 3; NaHCO$_3$, 25; CaCl$_2$, 2.5; MgCl$_2$, 0.5; glucose, 12. The combined solutions were mechanically agitated for 3-5 minutes and then held in a thermo-neutral sonicator until use.

Example 4

Preparation of Anesthetic Compositions Comprising an Extractive Solvent

The following solutions were prepared. Isoflurane was obtained. NMP was obtained from Sigma-Aldrich Chemical company. A 40% (v/v) isoflurane-NMP solution was made adding 40 ml of isoflurane to 60 ml of NMP. A 40% (v/v) isoflurane-ethanol solution was made adding 40 ml of isoflurane to 60 ml of ethanol.

Saline compositions with varying concentrations of isoflurane and NMP were made by mixing the above NMP-isoflurane solution with saline as follows:

| Sample | Saline (ml) | Base-Isoflurane Compositions (ml) | % Isoflurane | % NMP |
|---|---|---|---|---|
| A | 0 | 10 | 40% | 60% |
| B | 2 | 8 | 32 | 48 |
| C | 4 | 6 | 24 | 36 |
| D | 5 | 5 | 20 | 30 |
| E | 6 | 4 | 16 | 24 |
| F | 8 | 2 | 8 | 12 |
| G | 10 | 0 | 0 | 0 |

Control compositions with varying concentrations of isoflurane-ethanol were made by mixing the above isoflurane-ethanol compositions with saline as follows:

| Sample | Saline (ml) | Control-Isoflurane Compositions (ml) | % Isoflurane | % Ethanol |
|---|---|---|---|---|
| H | 0 | 10 | 40% | 60% |
| I | 2 | 8 | 32 | 48 |
| J | 4 | 6 | 24 | 36 |
| K | 5 | 5 | 20 | 30 |
| L | 6 | 4 | 16 | 24 |
| N | 8 | 2 | 8 | 12 |
| M | 10 | 0 | 0 | 0 |

To determine the stability of the compositions, the following experiment may be performed. Each sample is divided into two containers containing 5 mls of the sample. One of the samples is capped. The other sample is left uncapped. Over time (1 hour, 6 hour, 24 hour, etc.), the samples are examined to see if the isoflurane has separated from solution. Furthermore, the concentration of isoflurane in each solution may be determined at each time point. The uncapped sample may be compared to the capped sample to determine the stability of the solution. Furthermore, the isoflurane-NMP compositions may then be compared to the control compositions. It is anticipated that the anesthetic compositions will remain miscible at all concentrations.

Example 5

Preparation of Anesthetic Compositions Comprising an Emulsion

Solutions of emulsified isoflurane are prepared at room temperature (20° C.) by adding liquid isoflurane to 30% Intralipid® (Sigma-Aldrich) in gas-tight glass bottles fitted with Teflon stoppers. The bottles are then vibrated on a vibrator at 50 Hz for 30 minutes. (For examples see, Zhou et al, 2006, Anesth Analg 102:129-34; Taheri et al., 1991, Anesth Analg 1991; 72:627-34).

| Sample | 30% Intralipid (ml) | Isoflurane (ml) | % Isoflurane |
|---|---|---|---|
| A | 40 | 1.28 | 3.1 |
| B | 40 | 2.55 | 6.0 |
| C | 40 | 3.48 | 8.0 |
| D | 40 | 4.45 | 10.0 |
| E | 40 | 10.0 | 20.0 |
| F | 40 | 26.67 | 40.0 |

To determine the stability of the compositions, the following experiment is performed. Each sample is divided into two containers containing 5 ml of the sample. One of the samples is capped. The other sample is left uncapped. Over time (1 hour, 6 hour, 24 hour, etc.), the samples are examined to see whether the isoflurane has separated from solution, or whether the lipid phase has separated from the aqueous phase. Furthermore, the concentration of isoflurane in each solution may be determined at each time point. The uncapped sample may be compared to the capped sample to determine the stability of the solution. It is anticipated that the anesthetic compositions will not separate at all concentrations.

One of skill in the art will realize that emulsions of isoflurane may be made using other lipids, including other emulsion preparations, such as 10% (w/v) Intralipid® or 20% (w/v) Intralipid®, using variations of the methods described herein. Other commercially available lipid compositions that may be useful for the production of the volatile anesthetic compositions of the present invention include, but are not limited to, Liposyn® (B. Braun) and Nutrilipid® (13. Braun).

One of skill in the art will also realize that emulsions of desflurane, sevoflurane, isoflurane, enflurane, methoxyflurane and halothane may be produced using variations of the methods described herein.

Example 6

Preparation of Anesthetic Compositions Comprising an Extractive Solvent and an Emulsion The following solutions and emulsions are prepared. Isoflurane is obtained. NMP is obtained from Sigma-Aldrich Chemical company. A 40% (v/v) isoflurane-NMP solution is made by adding 40 ml of isoflurane to 60 ml of NMP (as in Example 4).

Emulsion compositions with varying concentrations of isoflurane and NMP are prepared by mixing the above NMP-isoflurane solution with 30% Intralipid (Sigma-Aldrich) at room temperature (20° C.) in gas-tight bottles fitted with Teflon stoppers as follows:

| Sample | 30% Intralipid (ml) | 40% (v/v) isoflurane-NMP (ml) | % Isoflurane | % NMP |
| --- | --- | --- | --- | --- |
| A | 40 | 3.37 | 3.1 | 4.7 |
| B | 40 | 7.06 | 6.0 | 9.0 |
| C | 40 | 10.0 | 8.0 | 12.0 |
| D | 40 | 13.34 | 10.0 | 15.0 |
| E | 40 | 40.0 | 20.0 | 30.0 |

After mixing, the bottles are vibrated on a vibrator at 50 Hz for 30 minutes. To determine the stability of the compositions, the following experiment is performed. Each sample is divided into two containers containing 5 ml of the sample. One of the samples is capped. The other sample is left uncapped. Over time (1 hour, 6 hour, 24 hour, etc.), the samples are examined to see whether the isoflurane has separated from solution, or whether the lipid phase has separated from the aqueous phase. Furthermore, the concentration of isoflurane in each solution is determined at each time point. The uncapped sample may be compared to the capped sample to determine the stability of the solution. It is anticipated that the anesthetic compositions will not separate at all concentrations.

One of skill in the art will realize that emulsions of isoflurane may be made using other lipids, including other emulsion preparations, such as 10% (w/v) Intralipid® or 20% (w/v) Intralipid®, using variations of the methods described herein. Other commercially available lipid compositions that may be useful for the production of the volatile anesthetic compositions of the present invention include, but are not limited to, Liposyn® (B. Braun) and Nutrilipid® (B. Braun).

One of skill in the art will also realize that emulsions of desflurane, sevoflurane, isoflurane, enflurane, methoxyflurane and halothane may be produced using variations of the methods described herein.

Example 7

Stability of Isoflurane Formulations

In the Examples that follow, the stability of isoflurane in the described compositions was determined in two ways. First, the compositions were examined for the presence of phase separation at the macroscopic level. Secondly, isoflurane content of the compositions was determined by weighing the remaining isoflurane in the composition when they were left uncapped over time. Briefly, glass vials were filled with 5-10 ml of the composition vehicle and then weighed; one of them received only vehicle (i.e., no isoflurane) and served as control. The other vials received varying amounts of isoflurane. They were left uncapped in the hood. Over time, the vials were weighed to see if the isoflurane stayed in the composition or had evaporated. The amount evaporated over time in the vehicle control was subtracted from that in the isoflurane-containing composition.

The pure form of isoflurane is a volatile anesthetic. In order to assess the volatility of isoflurane, two vials received the indicated amounts of pure form isoflurane. The vials were placed in the chemical fume hood and left uncapped. The vials were weighed at the indicated times to determine the amount of evaporated isoflurane. As it is shown in the table below 0.7893 g isoflurane was evaporated within 3 hours, while 3.4825 g isoflurane took approximately 8 hrs to evaporate completely. These amounts of isoflurane are similar to the amounts of isoflurane that were used to prepare the isoflurane compositions in the Examples that follow.

| Pure form of isoflurane (g) | 0 h (% remaining iso) | 0.25 h (% remaining iso) | 1 h (% remaining iso) | 2 h (% remaining iso) | 3 h (% remaining iso) | 5 h (% remaining iso) | 7 h | 8 h |
| --- | --- | --- | --- | --- | --- | --- | --- | --- |
| 0.7893 | 100 | 85 | 52 | 14 | 0 | | | |
| 3.4825 | 100 | 96 | 86 | 75 | 62 | 38 | 13 | 3 |

Example 8

Preparation of Isoflurane Solution (v/v) with NMP

Pure isoflurane USP (Forane) liquid was mixed with NMP (Sigma-Aldrich) in the indicated concentrations; the mixture was vortexed vigorously to prepare homogenous isoflurane-NMP solution. In order to reduce the amount of NMP in the solution, saline (0.9% NaCl) was added to the mixture.

| | NMP (%) | Saline (%) | Isoflurane (%) | Appearance of solutions |
|---|---|---|---|---|
| 1 | 90 | — | 10 | Clear |
| 2 | 60 | — | 40 | Clear |
| 3 | 63 | 27 | 10 | Clear |
| 4 | 72 | 20 | 8 | Clear |

| Isoflurane concentration in NMP | 0 h (% remaining iso) | 0.25 h (% remaining iso) | 1 h (% remaining iso) | 16 h (% remaining iso) | 24 h (% remaining iso) |
|---|---|---|---|---|---|
| 10 | 100 | 99 | 99 | 94 | 91 |
| 30 | 100 | 99 | 98 | 90 | 86 |

As it is shown in the tables above, 10% and 40% of isoflurane was mixed with NMP, and the resulting solution looked clear. Moreover, the addition of NMP reduced the volatility of isoflurane, as compared with Example 7.

Example 9

Preparation of Emulsified Isoflurane (V/V) in Intralipid

Pure isoflurane USP (Forane) liquid is mixed with Intralipid 20% or 30% (Baxter) at the indicated concentrations; the mixture was vortexed vigorously and sonicated for 30 minutes to prepare homogenous isoflurane-intralipid emulsion.

| | Lipid Emulsion | Isoflurane Concentration | Appearance of Emulsions |
|---|---|---|---|
| 1 | 20% Intralipid | 1-6% | Homogenous |
| 2 | 30% intralipid | 6-10% | Homogenous |

| Isoflurane concentration in intralipid 20% | 0 h (% remaining iso) | 0.25 h (% remaining iso) | 1 h (% remaining iso) | 16 h (% remaining iso) | 24 h (% remaining iso) |
|---|---|---|---|---|---|
| 2 | 100 | 95 | 95 | 92 | 91.7 |
| 3 | 100 | 93 | 92 | 70 | 69.8 |
| 4 | 100 | 94 | 92 | 55 | 55.3 |
| 5 | 100 | 96 | 95 | 60 | 58.9 |

Intralipid emulsions with the indicated amount of isoflurane looked homogenous and uniform. Moreover, intralipid reduced the volatility of isoflurane, as compared with Example 7.

One of skill in the art will realize that emulsions of isoflurane may be made using other lipids, including other emulsion preparations, such as 10% (w/v) Intralipid, using variations of the methods described herein. Other commercially available lipid compositions that may be useful for the production of the volatile anesthetic compositions of the present invention include, but are not limited to, Liposyn® (B. Braun) and Nutrilipid® (B. Braun). One of skill in the art will also realize that emulsions of desflurane, sevoflurane, isoflurane, enflurane, methoxyflurane and halothane may be produced using variations of the methods described herein.

Example 10

Preparation of Emulsified Isoflurane (v/v) in Intralipid and NMP

Pure isoflurane USP (Forane) liquid is mixed with NMP (Sigma-Aldrich) in the indicated concentrations; the NMP-Isoflurane solution was added to intralipid 20% or 30% (Baxter). The mixture was vortexed vigorously and sonicated for 30 minutes to prepare homogenous isoflurane-NMP-intralipid emulsion.

| | 20% Intralipid (%) | NMP (%) | Isoflurane (%) | Appearance of emulsions |
|---|---|---|---|---|
| 1 | 75 | 15 | 10 | Homogenous |
| 2 | 80 | 10 | 10 | Homogenous |

| Vehicle | Isoflurane (%) | 0 h (% remaining iso) | 0.25 h (% remaining iso) | 1 h (% remaining iso) | 16 h (% remaining iso) | 24 h (% remaining iso) |
|---|---|---|---|---|---|---|
| 20% intralipid + 15% NMP | 5 | 100 | 98 | 94 | 88 | 85 |
| 20% intralipid + 15% NMP | 10 | 100 | 98 | 97 | 93 | 89 |

Intralipid emulsions with the indicated amount of isoflurane in the presence of NMP looked homogenous and uniform. In the presence of NMP, intralipid was able to hold more isoflurane than in the absence of NMP, as compared with Example 7. In addition, the combination of intralipid and NMP reduced the volatility of isoflurane, as compared with Example 7.

One of skill in the art will realize that emulsions of isoflurane may be made using other lipids, including other emulsion preparations, such as 10% (w/v) intralipid, using variations of the methods described herein. Other commercially available lipid compositions that may be useful for the production of the volatile anesthetic compositions of the present invention include, but are not limited to, Liposyn® (B. Braun) and Nutrilipid® (B. Braun). One of skill in the art will also realize that emulsions of desflurane, sevoflurane, isoflurane, enflurane, methoxyflurane and halothane may be produced using variations of the methods described herein.

Example 11

Preparation of Polysorbate 80 (Tween 80)-Based Emulsified Isoflurane

Isoflurane was added to Tween 80 (3% v/v) for a total volume of 10 ml. The mixture was vortexed vigorously and sonicated for 30 minutes to prepare homogenous isoflurane emulsion. In some cases, 1,2-dimyristoyl-sn-glycero-3-phophocholine (DMPC) was included in the formulation. First, DMPC (0.3% or 0.6%) was dissolved in Tween 80 (3% v/v), then isoflurane was added to the Tween-DMPC mixture, which was followed by 30 minutes of sonication.

| | 3% Tween 80 (%) | DMPC (%) | Isoflurane (%) | Appearance of emulsions |
|---|---|---|---|---|
| 1 | 95 | — | 5 | Homogenous |
| 2 | 93 | 0.3 | 7 | Homogenous |
| 3 | 93 | 0.6 | 7 | Homogenous |

| Vehicle | Isoflurane (%) | 0 h (% remaining iso) | 0.25 h (% remaining iso) | 1 h (% remaining iso) | 16 h (% remaining iso) | 24 h (% remaining iso) |
|---|---|---|---|---|---|---|
| 3% Tween | 7 | 100 | 97 | 95 | 91 | 85 |
| 3% Tween + 0.3% DMPC | 7 | 100 | 98 | 96 | 94 | 89 |
| 3% Tween + 0.6% DMPC | 7 | 100 | 100 | 100 | 99 | 94 |

Tween 80-based emulsions appeared homogenous. When DMPC was added, the same amount of Tween 80 was able to hold more isoflurane than without DMPC. Moreover, the combination of isoflurane with Tween 80 or Tween 80 DMPC reduced the volatility of isoflurane, as compared with Example 7.

Example 12

Preparation of Isoflurane Solution (v/v with Propylene Glycol

Pure isoflurane USP (Forane) liquid was mixed with Propylene Glycol (Sigma-Aldrich) at the indicated concentrations; the mixture was vortexed vigorously to prepare homogenous isoflurane-Propylene Glycol solution.

| | Propylene Glycol (%) | Saline (%) | Isoflurane (%) | Appearance of solutions |
|---|---|---|---|---|
| 1 | 90 | — | 10 | Clear |
| 2 | 70 | — | 30 | Clear |
| 3 | 72 | 20 | 8 | Clear |

| Isoflurane concentration in Propylene Glycol | 0 h (% remaining iso) | 0.25 h (% remaining iso) | 1 h (% remaining iso) | 16 h (% remaining iso) | 24 h (% remaining iso) |
|---|---|---|---|---|---|
| 10 | 100 | 89 | 86 | 44 | 23 |
| 30 | 100 | 94 | 90 | 53 | 35 |

Eight percent, 10% and 30% of isoflurane was mixed with propylene glycol, and the resulting solutions appeared clear. Moreover, propylene glycol reduced the volatility of isoflurane, as compared with Example 7.

Example 13

Preparation of Cremophor EL-Based Emulsified Isoflurane

Isoflurane was added to an aqueous solution of Cremophor EL (10% v/v) for a total volume of 10 ml. The mixture was vortexed vigorously and sonicated for 30 minutes to prepare homogenous isoflurane emulsion.

| | 10% Cremophor EL (%) | Isoflurane (%) | Appearance of the emulsion |
|---|---|---|---|
| 1 | 95 | 5 | Milky |
| 2 | 90 | 10 | Milky |

| Vehicle | Isoflurane Concentration | 0 h (% remaining iso) | 0.25 h (% remaining iso) | 1 h (% remaining iso) | 16 h (% remaining iso) | 24 h (% remaining iso) |
|---|---|---|---|---|---|---|
| 10% Cremophor | 5 | 100 | 90 | 85 | 68 | 54 |
| 10% Cremophor | 10 | 100 | 91 | 87 | 73 | 60 |

Cremophor EL-based emulsions with the indicated amount of isoflurane appeared milky. Moreover, the Cremophor EL-based emulsions reduced the volatility of isoflurane, as compared with Example 7.

Example 14

Preparation of Isoflurane Solution (V/V) with Dimethyl Sulfoxide (DMSO)

Pure isoflurane USP (Forane) liquid was mixed with DMSO (BDH) at the indicated concentrations. The mixture was vortexed vigorously to prepare homogenous isoflurane-DMSO solution. The isoflurane solutions containing DMSO appeared clear.

| | DMSO (%) | Saline (%) | Isoflurane (%) | Appearance of solutions |
|---|---|---|---|---|
| 1 | 90 | — | 10 | Clear |
| 2 | 50 | — | 50 | Clear |
| 3 | 72 | 20 | 8 | Clear |

Example 15

Preparation of Isoflurane Solution (V/V) in Perfluorooctyl Bromide

Pure isoflurane USP (Forane) liquid was mixed with Perfluorooctyl Bromide (Acros Organics) at the indicated concentrations. The mixture was vortexed vigorously to prepare homogenous isoflurane-Perfluorooctyl Bromide solution. The isoflurane solutions containing Perfluorooctyl Bromide appeared clear.

| | Perfluorooctyl Bromide (%) | Isoflurane (%) | Appearance of solutions |
|---|---|---|---|
| 1 | 90 | 10 | Clear |
| 2 | 80 | 20 | Clear |

Example 16

Preparation of Isoflurane Solution (V/V) in PEG 400

Isoflurane (2 mL) was mixed with PEG-400 (2 mL) in a vial and contents were shaken resulting in a clear solution. The volatility of the resulting solution was compared to the volatility of pure isoflurane using Exetech Heavy Duty Differential Pressure Manometer Model 407910. At least a 3 fold reduction of vapor pressure was observed when heated to about 39° C.

Example 17

Preparation of Isoflurane Solution (V/V) in PEG 300

Isoflurane (2 mL) was mixed with PEG-300 (2 mL) in a vial and contents were shaken resulting in a clear solution. The volatility of the resulting solution was compared to the volatility of pure isoflurane using Exetech Heavy Duty Differential Pressure Manometer Model 407910. At least a 3 fold reduction of vapor pressure was observed when heated to about 39° C.

Example 18

Preparation of Isoflurane Solution (V/V) in Diethylene Glycol Monoethyl Ether

Isoflurane (2 mL) was mixed with diethylene glycol monoethyl ether (2 mL) in a vial and contents were shaken resulting in a clear solution. The volatility of the resulting solution was compared to the volatility of pure isoflurane using Exetech Heavy Duty Differential Pressure Manometer Model 407910. At least a 3 fold reduction of vapor pressure was observed when heated to about 39° C.

The disclosures of each and every patent, patent application, and publication cited herein are hereby incorporated herein by reference in their entirety.

All of the compositions and methods disclosed and claimed herein may be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating or reducing inflammation in a subject in need thereof, said method comprising administering to said subject a composition comprising a construct in an amount effective to treat or reduce said inflammation, wherein said construct is selected from the group consisting of:
   (a) a volatile anesthetic dissolved in a solution, wherein said solution further comprises at least one extractive solvent in an amount effective to reduce volatility of said volatile anesthetic, and
   (b) a micro-droplet suspension comprising a sphere of a volatile anesthetic surrounded by a stabilizing layer of a phospholipid;
   wherein said administration is topical, mucosal, rectal, vaginal, or buccal; and wherein the at least one extractive solvent is selected from the group consisting of dimethyl sulfoxide (DMSO), dimethylformamide (DMF), dimethylacetamide (DMA), N-methyl-2-pyrrolidone (NMP), dimethylisosorbide, ethanol, propanol, PEG-400, PEG-300, diethylene glycol monoethyl ether, and isopropanol, and
   wherein said volatile anesthetic is selected from the group consisting of isoflurane, halothane, enflurane, sevoflurane, desflurane, methoxyflurane, and mixtures thereof.

2. The method of claim 1, wherein said inflammation is associated with arthritis, tendonitis, bursitis, colitis, inflammatory bowel disease, iritis, polymyositis, interstitial cystitis, inflammatory chronic prostatitis, inflammatory breast cancer (IBC) or vasculitis.

* * * * *